US011674914B2

(12) United States Patent
Hutchinson et al.

(10) Patent No.: US 11,674,914 B2
(45) Date of Patent: Jun. 13, 2023

(54) IMPEDANCE SENSOR

(71) Applicant: Baker Hughes Holdings LLC, Houston, TX (US)

(72) Inventors: Andrew Walter Hutchinson, Richmond, VA (US); James Michael Lustig, Newbury, OH (US); Scott Anderson, Clinton, OH (US); Claudia Leon, Houston, TX (US); Edward Baus, Akron, OH (US)

(73) Assignee: Baker Hughes Holdings LLC, Houston, TX (US)

( * ) Notice: Subject to any disclaimer, the term of this patent is extended or adjusted under 35 U.S.C. 154(b) by 25 days.

(21) Appl. No.: 17/527,303

(22) Filed: Nov. 16, 2021

(65) Prior Publication Data
US 2023/0152261 A1   May 18, 2023

(51) Int. Cl.
  *G01N 27/02*   (2006.01)
  *G01K 7/02*    (2021.01)
(52) U.S. Cl.
  CPC ............ *G01N 27/02* (2013.01); *G01K 7/02* (2013.01)
(58) Field of Classification Search
  None
  See application file for complete search history.

(56) References Cited

U.S. PATENT DOCUMENTS

| 6,915,703 | B2 | 7/2005 | Haase et al. |
| 8,279,194 | B2 | 10/2012 | Kent et al. |
| 10,801,985 | B2 * | 10/2020 | Cook ............... B82Y 30/00 |
| 2020/0011827 | A1 | 1/2020 | Zhou et al. |

FOREIGN PATENT DOCUMENTS

| WO | 2014030129 A1 | 2/2014 |
| WO | 2018087352 A1 | 5/2018 |

OTHER PUBLICATIONS

Rivadeneyra et al., "Recent Advances in Printed Capacitive Sensors", Micromachines (Basel), Apr. 2020, 1-20.
Shemelya et al., "3D printed capacitive sensors", Sensors, 2013 IEEE, Nov. 3-6, 2013, 1-4.

* cited by examiner

*Primary Examiner* — Raul J Rios Russo
*Assistant Examiner* — Carl F. R. Tchatchouang
(74) *Attorney, Agent, or Firm* — Mintz Levin Cohn Ferris Glovsky and Popeo, PC

(57) ABSTRACT

A sensor having a sensor head including a unibody construction, a first electrode, and at least one second electrode is provided. The first electrode can include a first pair of sensing elements coupled to each over via at least one bridge element extending from a first sensing element to a second sensing element. The at least one second electrode can include a second pair of sensing elements interleaved with the first pair of sensing elements. The second pair of sensing elements can be coupled to each other via at least one second bridge element extending from a third sensing element to a fourth sensing element. A method of manufacturing the sensor is also provided.

20 Claims, 21 Drawing Sheets

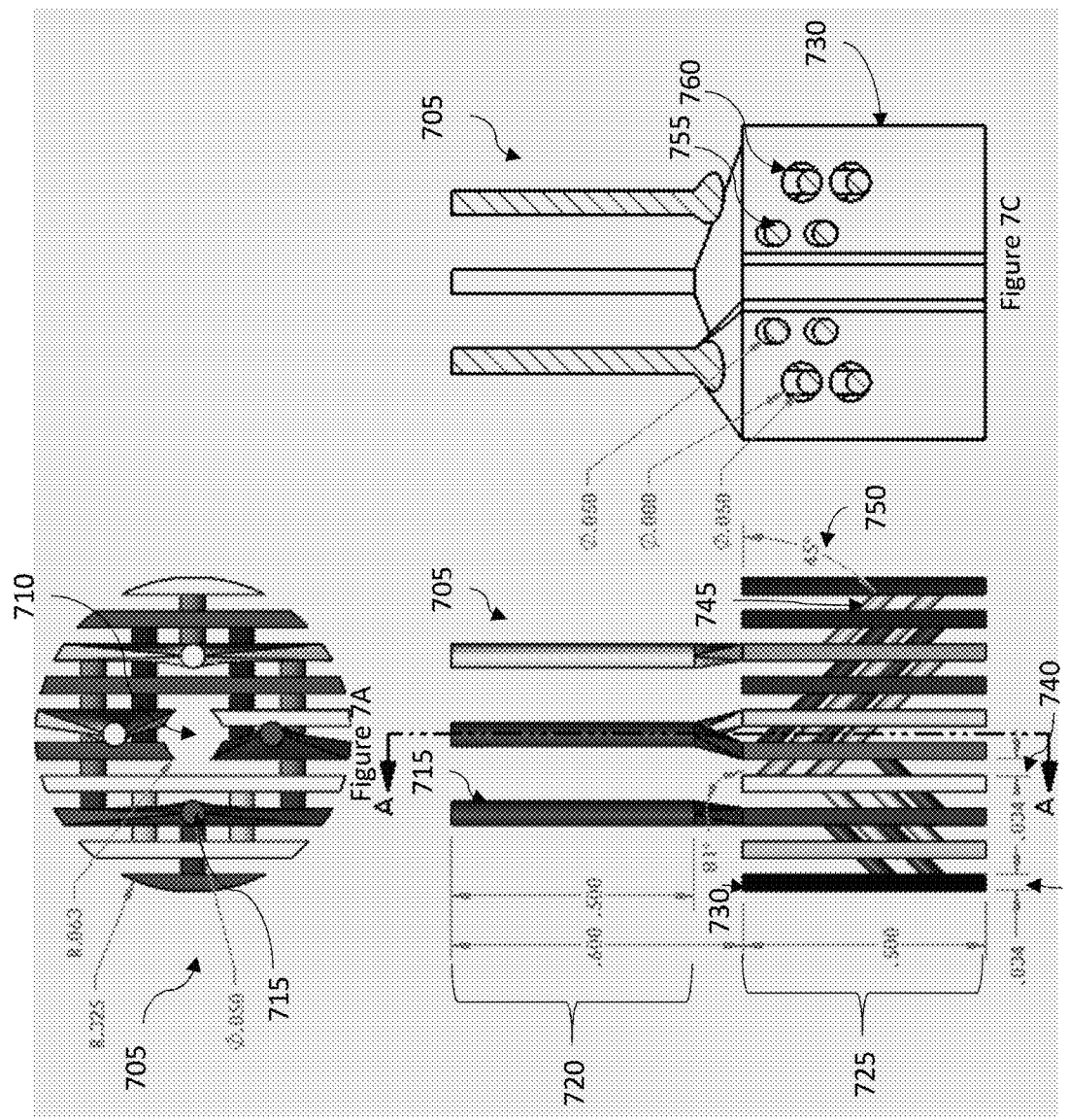

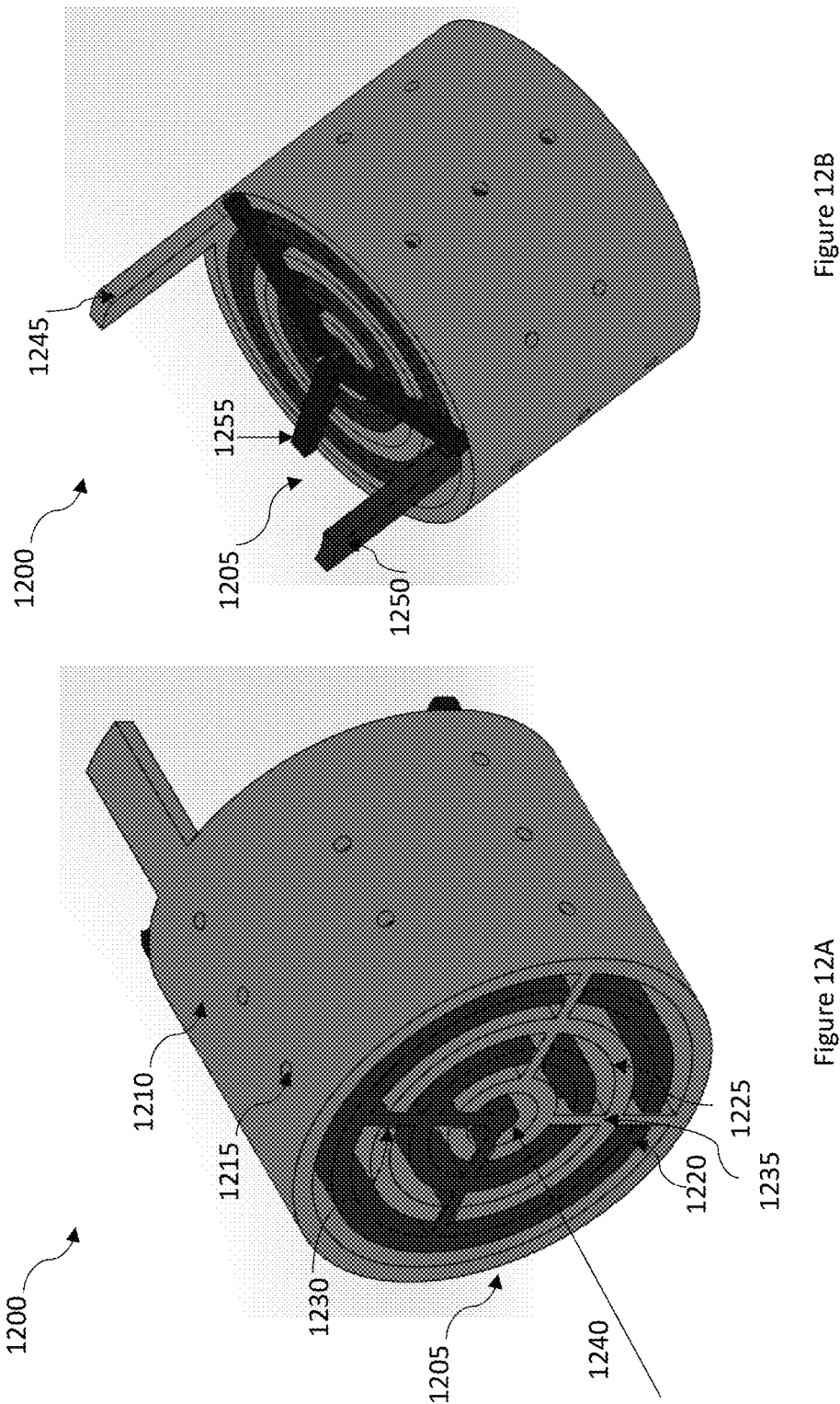

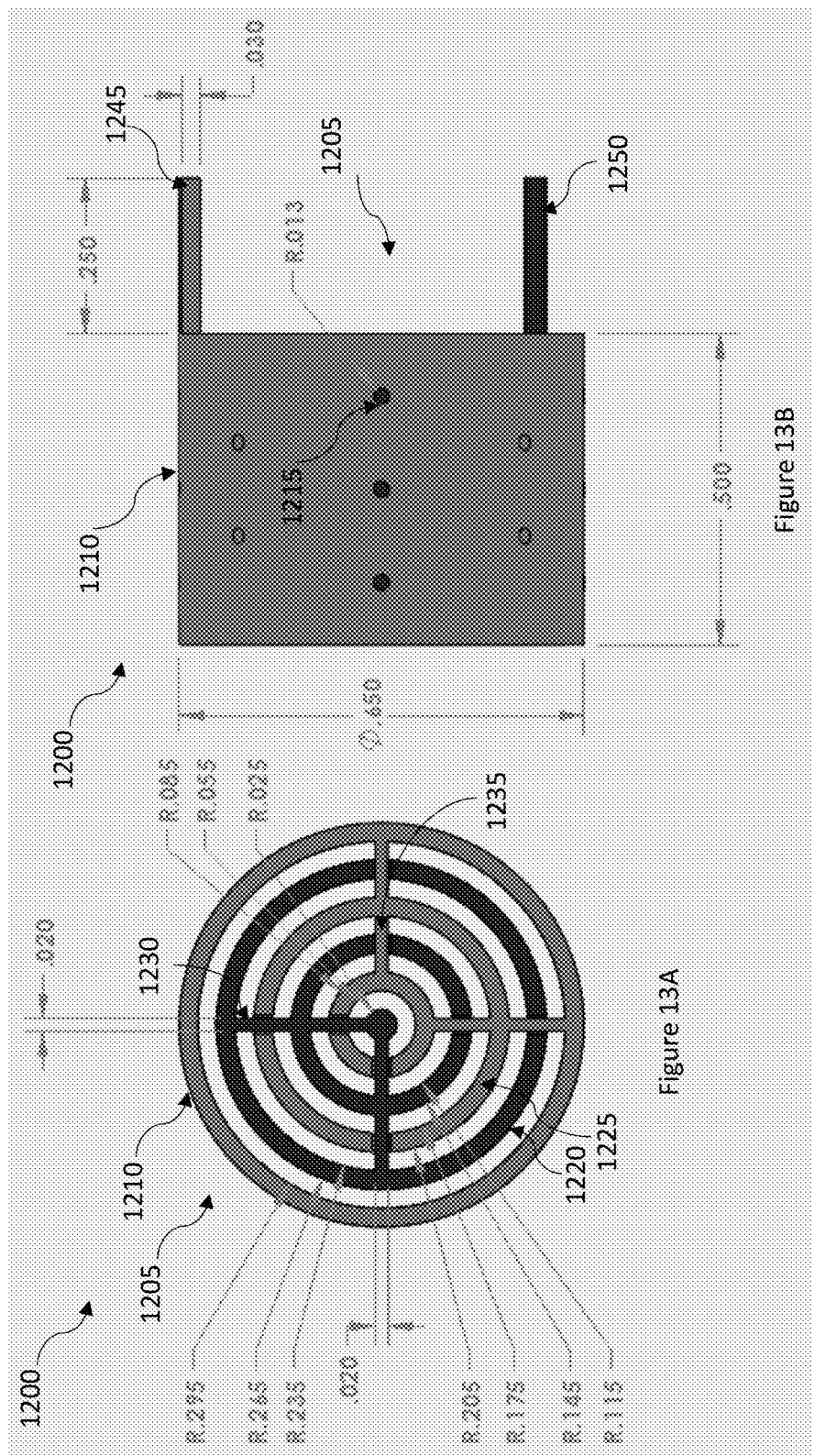

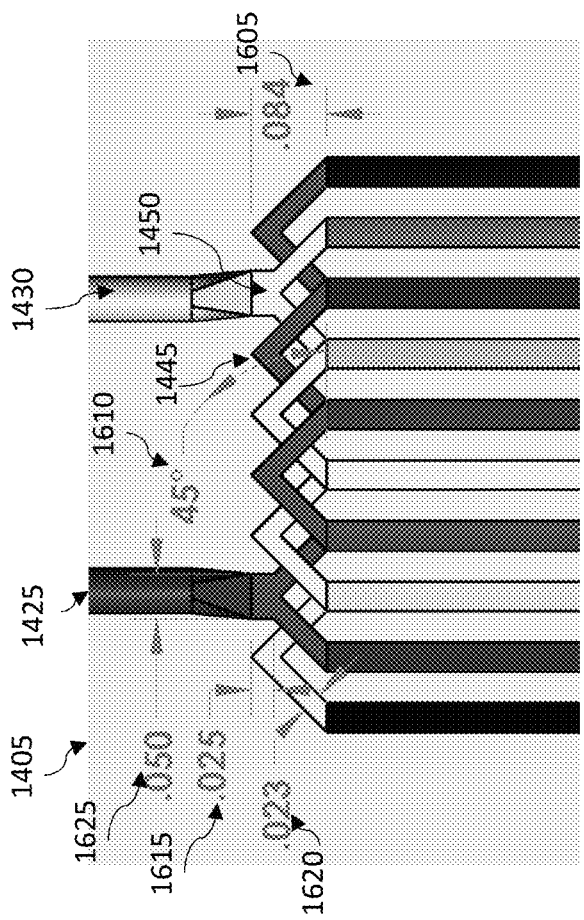
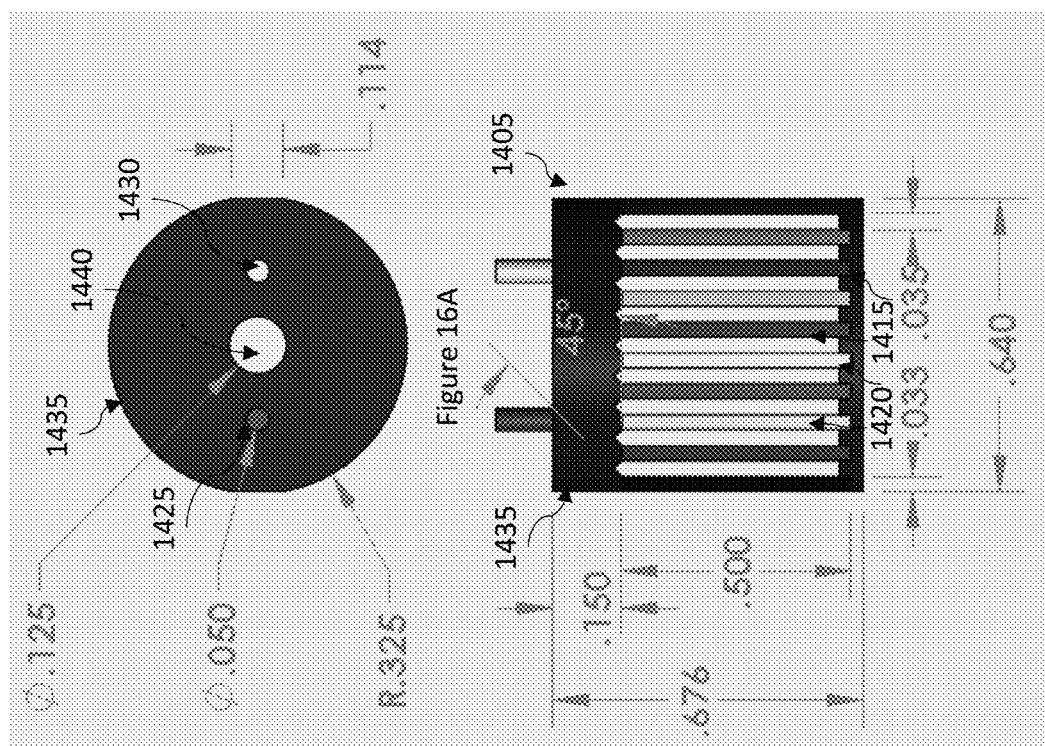
Figure 16C
Figure 16A
Figure 16B

IMPEDANCE SENSOR

TECHNICAL FIELD

The subject matter described herein relates to an impedance sensor formed via additive manufacturing techniques.

BACKGROUND

Sensors can be used to measure the quality of fluids, such as lubricants, circulating within industrial machinery. Fluids which have degraded or contain impurities can adversely affect the performance of the machinery and can cause the machinery to fail. An impedance sensor can be configured to measure the impedance of a fluid provided to, received from, or circulating within industrial machinery. Impedance sensors can include multiple, separate electrodes, which can be manufactured separately and assembled in complex configurations that can be costly to source, assemble, and troubleshoot. It can be advantageous to form an impedance sensor with an integral, unibody configuration that can provide optimal flow characteristics across larger surfaces areas to eliminate complex assembly of multiple separate components and to generate impedance data more accurately than existing impedance sensors.

SUMMARY

In one aspect, a sensor is provided. In an embodiment, the sensor can include a sensor head having a unibody construction and including a first electrode and at least one second electrode. The first electrode can include a pair of sensing elements coupled to each other via at least one bridge element extending form a first sensing element to a second sensing element. The first sensing element and the second sensing element can be included in the first pair of sensing elements. The at least one second electrode can include a second pair of sensing elements interleaved with the first paid of sensing elements. The second pair of sensing elements can be coupled to each other via at least one second bridge element extending from a third sensing element to a fourth sensing element. The third sensing element and the fourth sensing element can be included in the second pair of sensing elements.

In some variations, one or more features disclosed herein, including the following features, may option be included in any feasible combination. For example, the at least one first bridge element can extend through a pass-through feature of the third sensing element and the at least one second bridge element can extend through a pass-through feature of the second sensing element. The sensor can include a housing and a header. The sensor can include a base coupled to the first electrode and the second electrode. The sensor can include a thermocouple positioned between the first electrode and the second electrode. The sensor can be an impedance sensor. The impedance sensor can be installed in at least one of a combustion engine, a gear box, a gas turbine, a compressor, or a hydraulic system. The impedance sensor can be configured in an oil and gas production environment.

The first electrode or the second electrode can be formed from a non-conductive material and the first electrode or the second electrode can be coated with a conductive coating. The non-conductive material can be a ceramic. The first electrode and the second electrode can be interleaved in a planar manner to form a cylindrical shape. The first electrode and the second electrode can be interleaved in a planar manner to form a cubic shape. The first electrode and the second electrode can be interleaved in a concentric manner to form a cylindrical shape. The sensor can include a plurality of gaps between adjacent sensing elements of the first pair of sensing elements and the second pair of sensing elements. The plurality of gaps can be configured for a fluid to flow through the sensor. The fluid can be a lubricant, water, an oil, or a coolant.

In another aspect, a method of manufacturing is provided. In one embodiment, the method can include providing a first material and forming a sensor from the first material using an additive manufacturing technique. The sensor can include a sensor head having a unibody construction and including a first electrode and at least one second electrode. The first electrode can include a pair of sensing elements coupled to each other via at least one bridge element extending form a first sensing element to a second sensing element. The first sensing element and the second sensing element can be included in the first pair of sensing elements. The at least one second electrode can include a second pair of sensing elements interleaved with the first paid of sensing elements. The second pair of sensing elements can be coupled to each other via at least one second bridge element extending from a third sensing element to a fourth sensing element. The third sensing element and the fourth sensing element can be included in the second pair of sensing elements.

In some variations, one or more features disclosed herein, including the following features, may option be included in any feasible combination. For example, the additive manufacturing technique includes at least one of direct laser melting, direct metal laser melting, binder jetting, material jetting, powder bed fusion, or digital light processing. The first material can be a metal material or a ceramic material. The method can also include applying a conductive coating to the ceramic material.

DESCRIPTION OF DRAWINGS

These and other features will be more readily understood from the following detailed description taken in conjunction with the accompanying drawings, in which:

FIGS. 7A-7C are diagrams illustrating exemplary embodiments of sensing element pairs included in the sensor described according to the subject matter provided herein;

FIGS. 12A and 12B are diagrams illustrating isometric views of another embodiment of a sensor described according to the subject matter provided herein;

FIGS. 13A and 13B are top and side views, respectively, of the sensor of FIGS. 12A and 12B described according to the subject matter provided herein;

FIGS. 16A-16C are diagrams illustrating top, side, and close up views, respectively, of the sensor of FIGS. 14A and 14B described according to the subject matter provided herein;

It is noted that the drawings are not necessarily to scale. The drawings are intended to depict only typical aspects of the subject matter disclosed herein, and therefore should not be considered as limiting the scope of the disclosure.

DETAILED DESCRIPTION

Existing sensors for use in monitoring fluids in industrial machines can require assembly of multiple pieces and large inventories of specifically dimensioned components. It can be difficult to design a sensor, such as a fluid sensor or an impedance sensor, which has enough structural integrity and sensitivity for a broad range of applications. For example, capacitive sensors can be used to measure properties or characteristics of fluids. Capacitive sensors can require two parallel plates across which the fluid can flow. It can be desirable to have a large surface area of the plates and a small separation between plates so that a large volume of the fluid contacts the sensor. A variety of electrical components, such as the sensing plates, insulators, and supports can be required to adequately create a sensor sufficiently capable of providing effective sensing of fluid properties.

Forming a sensor using additive manufacturing techniques, such as 3D metal printing or laser sintering, can permit sensors of complex shapes to be formed by fusing metal powder into desired dimensions for a large variety of applications. The complex shapes can include interleaved or interlocking features, such as sensing elements, that can be fabricated in their final form without requiring assembly of multiple individual pieces. Additive manufacturing techniques can enable formation of unibody shaped sensors, as will be described herein, that include mechanical and electrical support components integrated into the unibody construction of the sensor. Additionally, the additive manufacturing techniques can enable formation of a sensor in a single manufacturing step, rather than requiring multiple assembly steps.

The sensor and method of manufacturing described herein can reduce assembly costs associated with welding components together. Also, the design of the sensing elements of the sensor is not constrained by inventory sizes or pre-existing shapes or costs of materials. As a result, non-conventional shapes can be used to overcome electrical, space, or structural integrity design requirements.

Embodiments of sensor and method of manufacturing are discussed herein in regard to use in an oil and gas production environment. However, embodiments of the disclosure can be employed for sensing characteristics of a fluid in any environment without limitation.

Figure 1B:
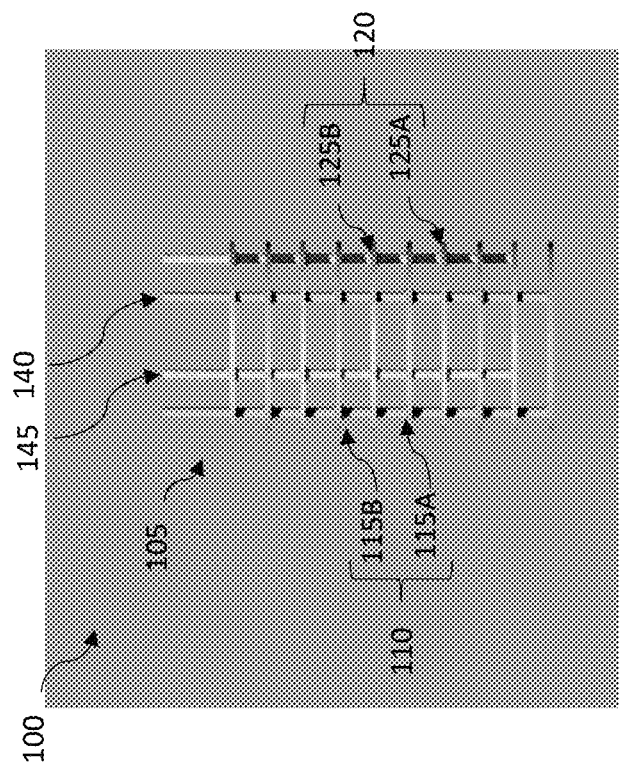
FIG. 1B is a diagram illustrating a side view of the embodiment of the sensor of FIG. 1A described according to the subject matter provided herein.
Figure 1A:
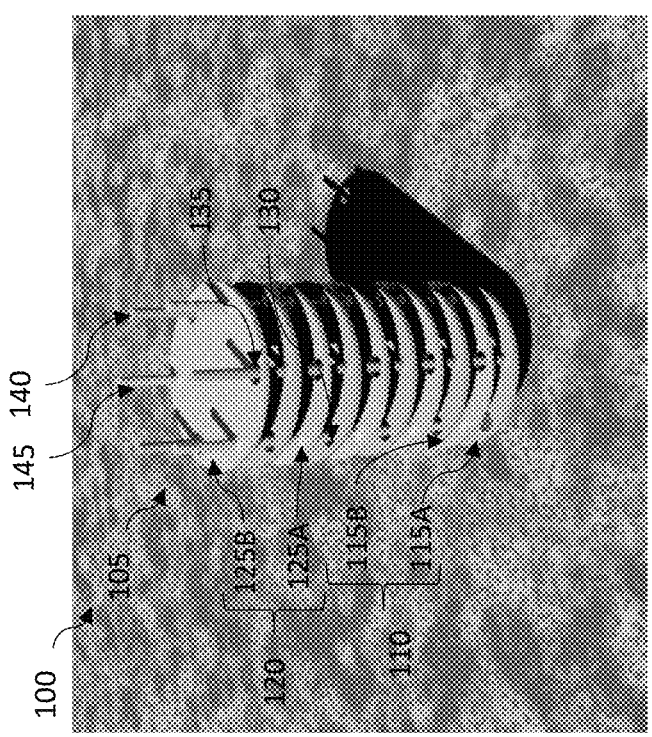
FIG. 1A is a diagram illustrating an isometric view of an embodiment of a sensor described according to the subject matter provided herein.

FIG. 1A is a diagram illustrating an isometric view of an embodiment of a sensor 100 described according to the subject matter provided herein. As shown in FIG. 1, the sensor 100 can include a sensor head 105. The sensor head can include a unibody construction, such that the features or components of the sensor head 105 are integrally formed within the sensor head and are not assembled from multiple pieces. The sensor head 105 can be formed to have a unibody construction using an additive manufacturing technique, which can form the sensor head 105 as a single, individual component from a single material or from a blend of materials.

The sensor head 105 can include a first electrode 110 and a second electrode 120. The first electrode 110 can include a pair of sensing elements, e.g., sensing element 115A and 115B. The sensing elements 115 can include a variety of shapes and geometries as will be described herein. For example, the sensing elements 115 can include circular, square, oval, rectangular, ellipsoid, or triangular shaped sensing elements. The second electrode 120 can also include a pair of sensing elements, such as sensing element 125A and 125B. The sensing elements 125 can include a variety of shapes and geometries as will be described herein. For example, the sensing elements 125 can include circular, square, oval, rectangular, ellipsoid, or triangular shaped sensing elements.

The sensing elements 115, 125 can include openings 130, 135 respectively. The openings 130, 135 can be holes, scalloped portions or features, pass-through features or portions, cut-away portions or features, or the like formed through or within the sensing elements 115, 125. The openings 130, 135 can allow a bridge element to pass through a sensing element so as to couple interleaved sensing elements that are associated with the same electrode together. For example, the bridge element 140 can be included in the electrode 110 and can extend from a first sensing element, such as sensing element 115A to a second sensing element, such as sensing element 115B. The bridge element 140 can extend through an opening 135 of a sensing element 125 of the second electrode 120. The second electrode 120 can also include a bridge element 145 extending from a sensing element 125 through an opening 130 in a sensing element 115 of the first electrode 110. The bridge elements 140, 145 can electrically couple the sensing elements 115, 125 of the electrodes 110, 120. The bridge elements 140, 145 can also provide structural rigidity to the sensor head 105.

The sensing elements 115 and 125 can be spaced apart from one another to maintain a gap between adjacent sensing elements 115, 125 so that a fluid can flow through the sensor head 105 and thus the sensor 100. The gap or spacing between adjacent sensing elements can be configured by the arrangement of the sensing elements coupled to the bridge elements. By allowing fluid to flow though sensor head 105, the sensor 100 can be used as an impedance sensor to measure characteristics of the fluid. For example, the sensor 100 can be utilized to measure acoustic or mechanical impedance of a fluid passing through it. In some embodiments the impedance sensor 100 can be installed in or coupled to industrial equipment, including but not limited to, a combustion engine, a gear box, a gas turbine, a compressor, a hydraulic system, or the like. In some embodiments, the industrial equipment can be included in an oil and gas production environment.

FIG. 1B is a diagram illustrating a side view of the embodiment of the sensor 100 of FIG. 1A described according to the subject matter provided herein. As shown in FIG. 1B, the sensor 100 includes a sensor head 105 that includes first electrodes 110 and second electrodes 120. One of the electrodes 110, 120 can be used as a ground circuit and another can be used as a sensing o signal circuit. The sensing elements 115, 125 can be interleaved between one another in a stacked formation and can be coupled to their respective bridge elements 140, 145 such that a gap or space is maintained between the individual sensing elements 115, 125.

Figure 2:
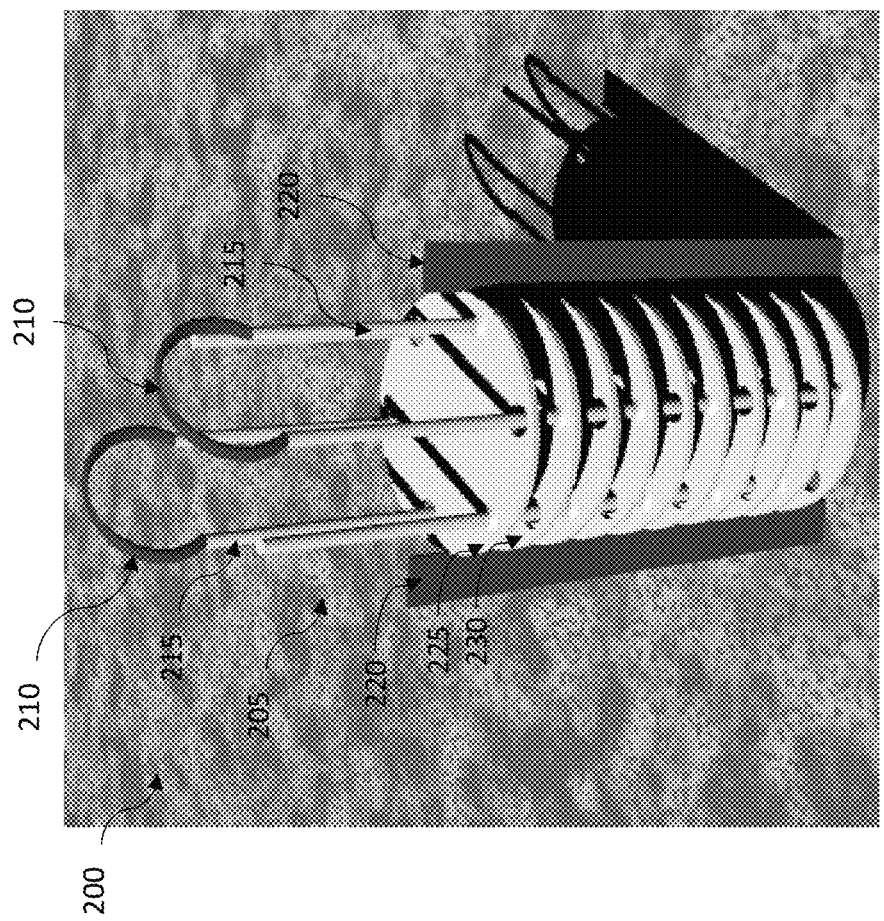
FIG. 2 is a diagram illustrating an isometric view of another embodiment of a sensor described according to the subject matter provided herein.

FIG. 2 is a diagram illustrating an isometric view of another embodiment of a sensor 200 described according to the subject matter provided herein. As shown in FIG. 2, the sensor 200 can include a sensor head 205. The sensor head 205 can be formed with one or more support structures during manufacturing to maintain the structural integrity of the unibody, integrated sensor head 205 as it is being formed via additive manufacturing techniques. For example, supports 210 can be formed to couple the bridge elements 215. The bridge elements 215 can correspond to the bridge elements 140, 145 described in relation to FIG. 1. Additionally, or alternatively, supports 220 can be formed to couple the sensing elements 225, 230. The sensing elements 225, 230 can correspond to the sensing elements 115, 125 of FIG. 1. A variety of configurations of the support structures can be envisioned coupling to either or both of the bridge elements 215 and/or the sensing elements 225, 230.

Figure 3:
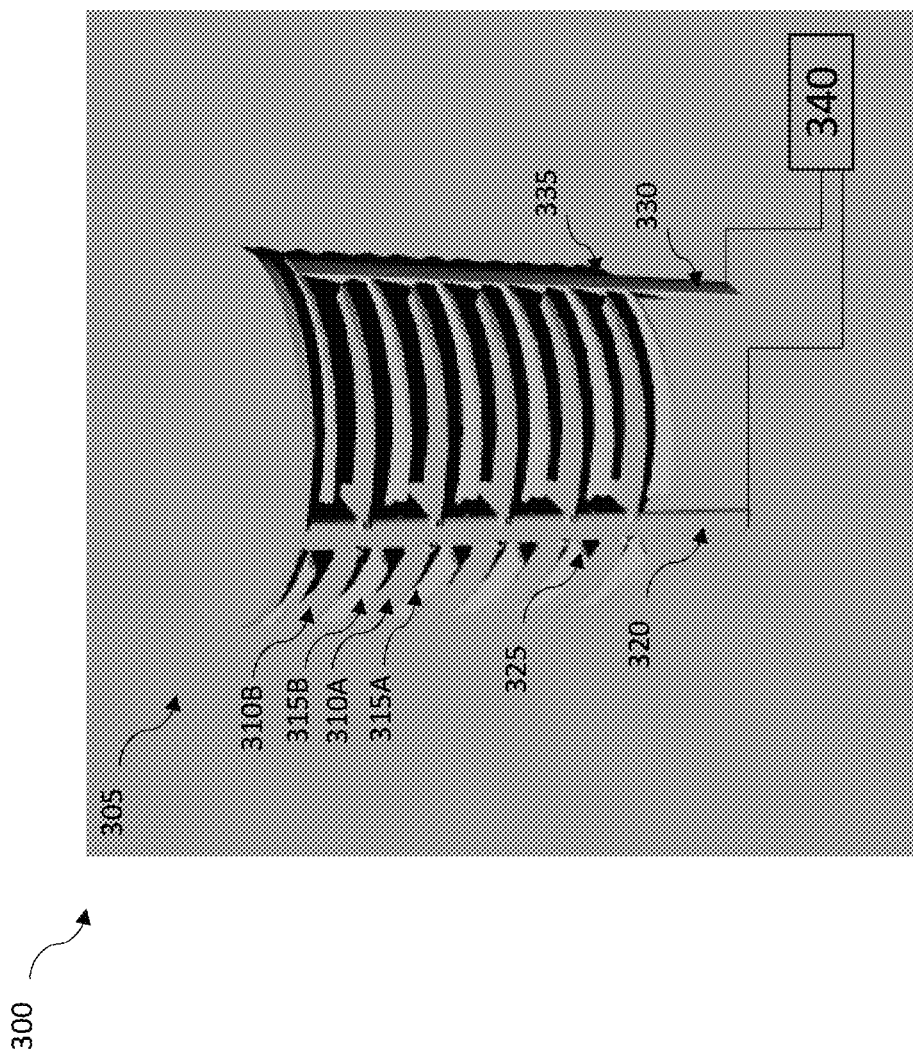
FIG. 3 is a diagram illustrating an isometric view of another embodiment of a sensor described according to the subject matter provided herein.

FIG. 3 is a diagram illustrating an isometric view of another embodiment of a sensor 300 described according to the subject matter provided herein. As shown in FIG. 3, the sensor head 305 can include interleaved pairs of sensing elements of a first electrode, 310A and 310B, which can be interleaved with interleaved pairs of sensing elements 315A and 315B of a second electrode. As shown in FIG. 3, the sensing elements 310 and 315 can each have a circular shape and can be arranged in a planar manner to stack the sensing elements 310 and 315 so as to form a cylindrically-shaped sensor 300.

As further shown in FIG. 3, the sensor head 305 can include bridge element 320 that can extend through pass-through 325 configured in one of the sensing elements 315. Similarly, the sensor head can include an additional bridge element 330 that can extend through pass-through 335 configured in one of the sensing elements 310. The pass-throughs 325, 335 can be cut-out portions of the sensing elements through which the bridge elements 320, 330 pass.

As further shown in FIG. 3, the sensor 300 can be coupled to an industrial machine 340. The industrial machine 340 can include a combustion engine, a gear box, a turbine, a compressor, a hydraulic system, or the like. The sensor 300 can be an impedance sensor coupled to a fluid circuit of the industrial machine 340 conveying a liquid or fluid, such as a lubricant or an oil therein. The sensor 300 can measure one or more properties of the fluid, such as a viscosity, an acoustic impedance, a mechanical impedance, or an electrochemical impedance of the fluid. The sensor 300 can operate at a frequency range between 0.1 Hz-100 kHz and can generate a voltage signal indicative of obtained measurements.

Figure 4:
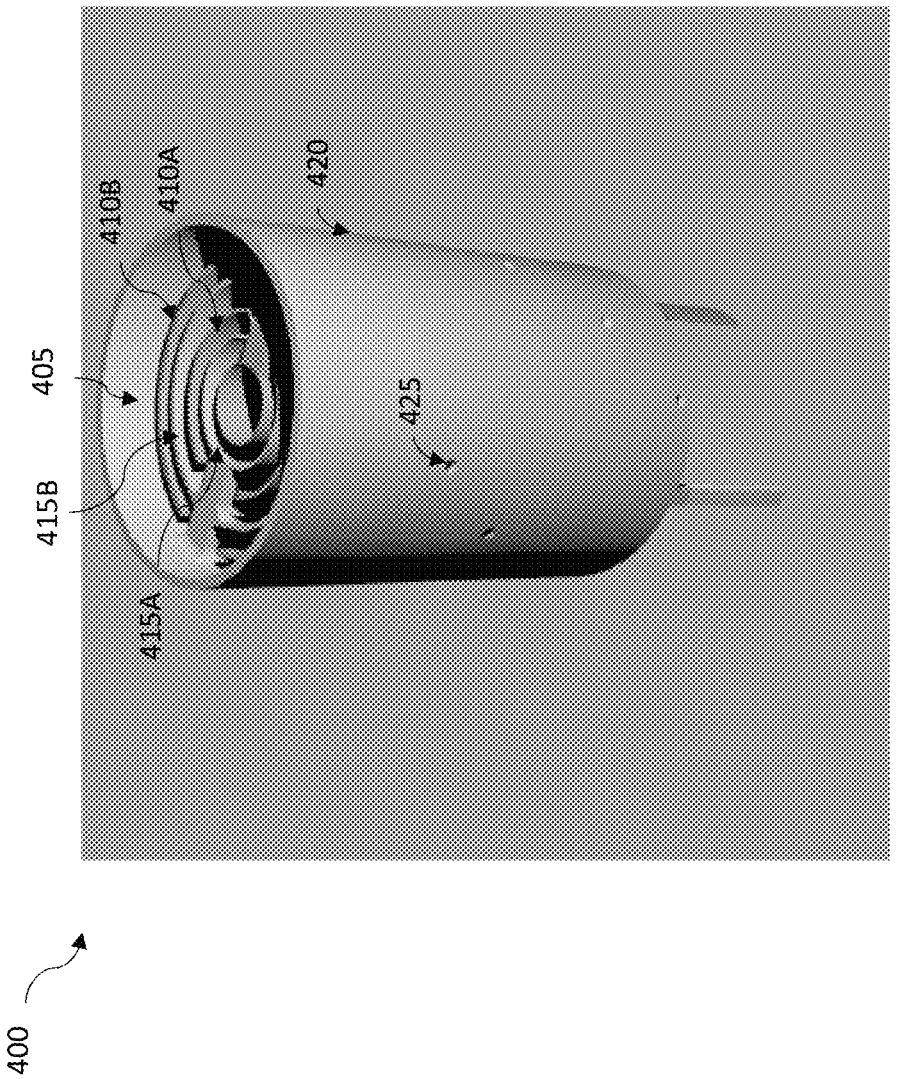
FIG. 4 is a diagram illustrating an isometric view of another embodiment of a sensor described according to the subject matter provided herein.

FIG. 4 is a diagram illustrating an isometric view of another embodiment of a sensor 400 described according to the subject matter provided herein. As shown in FIG. 4, the sensor head 405 can include an arrangement of interleaved sensing elements 410 included in a first electrode and sensing elements 415 included in a second electrode. The sensing elements 410 and 415 can be concentrically arranged such that the sensor 400 and the sensor head 405 includes a cylindrical shape.

As further shown, the sensor 400 can also include a housing 420. The housing 420 can be a shell or a sheath that can enclose the sensor head 405. The housing 420 can include one or more holes 425 in it to allow fluid to pass through the housing 420 and into the gaps formed in the sensor head 405 by the interleaved sensor elements 410, 415.

Figure 5B:
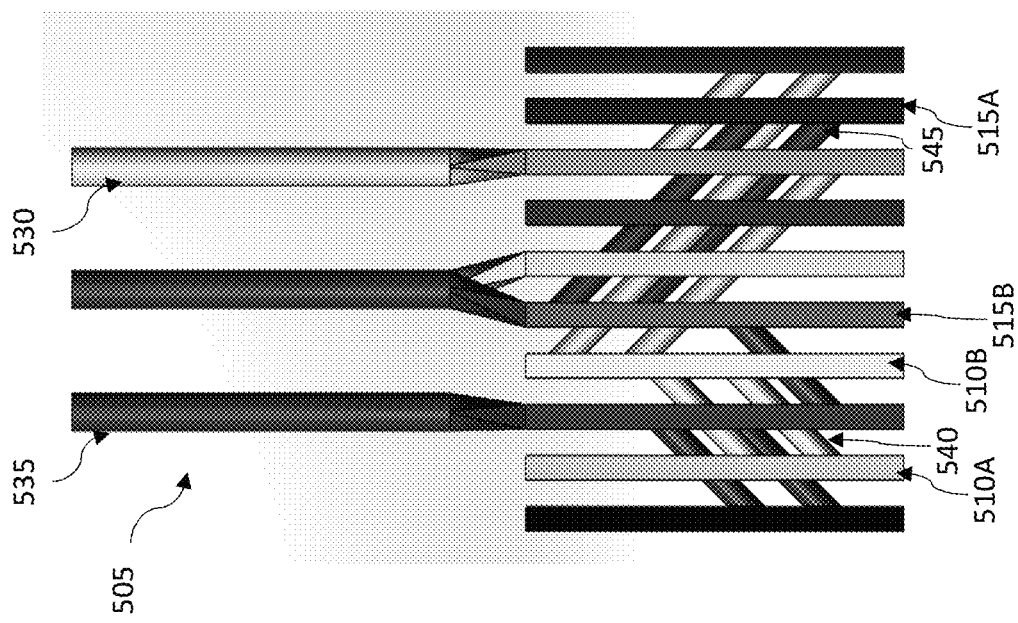
FIG. 5B is a diagram illustrating a close-up view of an embodiment of sensing element pairs included in a sensor described according to the subject matter provided herein.
Figure 5A:
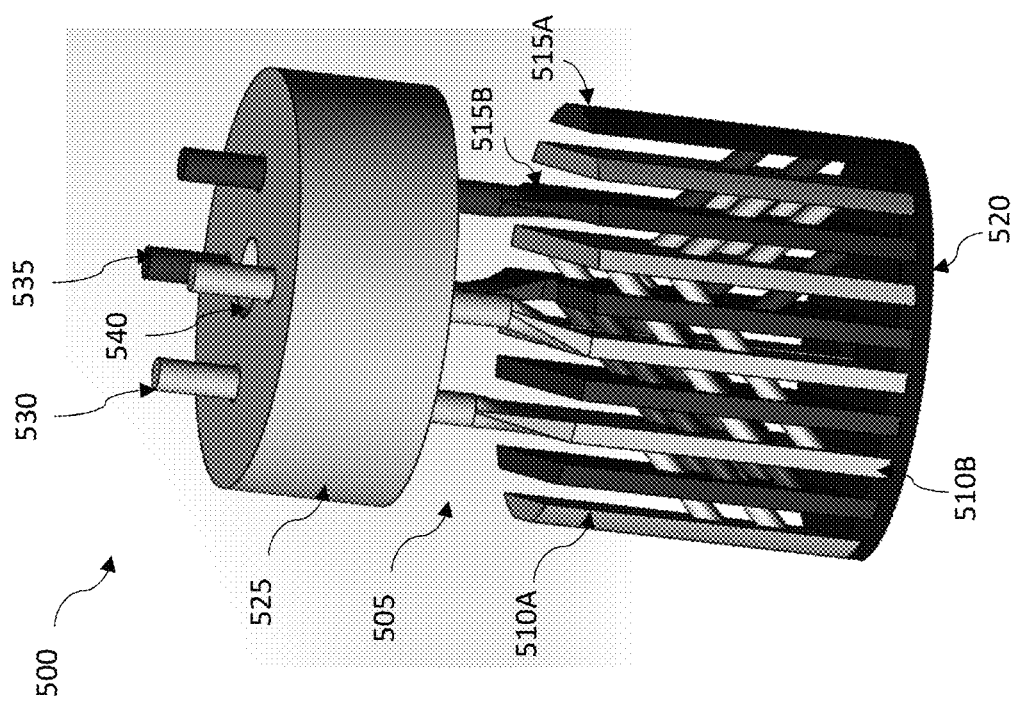
FIG. 5A is a diagram illustrating an isometric view of another embodiment of a sensor described according to the subject matter provided herein.

FIG. 5A is a diagram illustrating an isometric view of another embodiment of a sensor 500 described according to the subject matter provided herein. As shown in FIG. 5, the sensor head 505 can include a first plurality of sensing elements 510 (e.g., sensing elements 510A and 510B) forming a first electrode and a second plurality of sensing elements 515 (e.g., sensing elements 515A and 515B) forming a second electrode. The sensor head 505 can also include a base 520 to which the sensing elements 510, 515 are coupled. The base 520 can provide structural integrity to the sensing elements 510, 515. The base 520 can act as a spacer when the sensor head 505 is placed within a housing, such as the housing 420 described in relation to FIG. 4. As shown in FIG. 5A, the sensing elements 510 of the first electrode and the sensing elements 515 of the second electrode can be arranged in a planar manner to form the sensor head 505 with a cylindrical shape.

As further shown in FIG. 5A, the sensor head 505 can include a header 525. The header 525 can also provide structural integrity to the sensor head 505 and can include one or more holes for terminal ends 530 and 535 of the first and second electrodes to pass through the header 525. In some embodiments, the sensor head 505 can be brazed or welded in contact with the header 525. The header 525 can include a hole 540. The hole 540 can be configured to receive a measurement component, such as a thermocouple. When placed through the hole 540, the measurement component can be located between the first electrode formed from sensing elements 510) and the second electrode formed from sensing elements 515. In this way, the measurement component can be positioned between the first electrode and the second electrode.

FIG. 5B is a diagram illustrating a close-up view of an embodiment of sensing element pairs included in the sensor 500 described according to the subject matter provided herein. As shown in FIG. 5B, the sensor head 505, corresponding to sensor head 505 of FIG. 5A, includes bridge elements 540 and 545. For example, bridge element 540 can be included in a first electrode formed by the sensing elements 510A and 510B. Similarly, the bridge element 545 can be included in a second electrode formed by sensing elements 515A and 515B. A bridge element associated with a first a first electrode, such as bridge element 540 can extend from a first sensing element of the first electrode (e.g., sensing element 510A) through a pass-through feature, such as a hole or a cut-out portion, of one or more sensing elements of the second electrode to couple with another sensing element (e.g., sensing element 510B) of the first electrode. Bridge element 545 can similarly extend from sensing element 515A of a second electrode, through one or more sensing elements of the first electrode, and can couple with another sensing element 515B of the second electrode. In this way, the terminal ends 530 and 535 can be electrically coupled with each sensing element included in each respective electrode of the sensor head 505. Although the bridge elements 545 are shown in a diagonal orientation, other orientations, such as a horizontal orientation are also possible.

Figure 6:
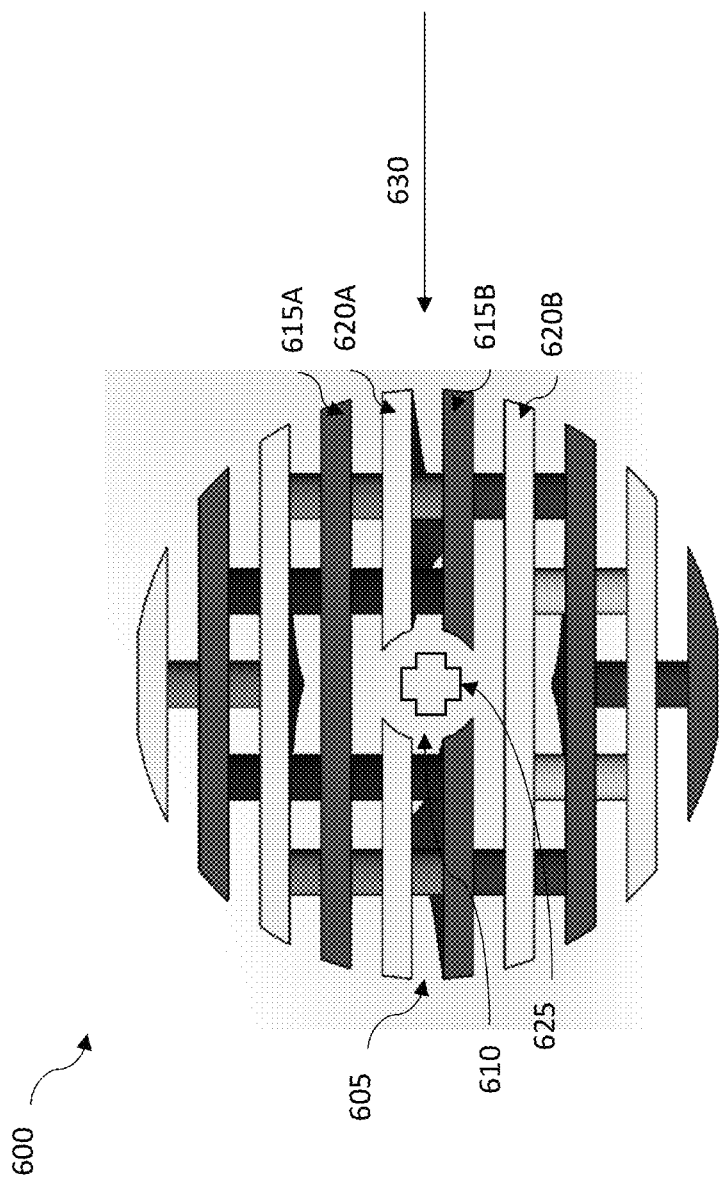
FIG. 6 is a diagram illustrating a bottom view of an embodiment of a sensor described according to the subject matter provided herein.

FIG. 6 is a diagram illustrating a bottom view of an embodiment of a sensor 600 described according to the subject matter provided herein. As shown in FIG. 6, the sensor head can include a hole 610 formed between sensing elements 615A, 615B of the first electrode and sensing elements 620A, 620B of the second electrode. A measurement component 625, such as a thermocouple, can be located in the hole 610 between the sensing elements of the first electrode and the second electrode. The measurement component 625 can measure properties or characteristics of a fluid 630 flowing through the gaps formed by the spacing of the sensor elements 615, 620 in the sensor head 605.

FIGS. 7A-7C are diagrams illustrating exemplary embodiments of sensing element pairs included in the sensor described according to the subject matter provided herein. As shown in the top down view of the sensor head 705 shown in FIG. 7A, the hole 710 can have a radius between 1.2 and 2.5 mm. The diameter 715 of the terminal ends 715 can between 0.7 and 2.5 mm. The radius of the sensor head 705 can be between 5.0 and 20.3 mm.

FIG. 7B is a side view of the sensor head 705 shown in FIG. 7A. The sensor head 705 can have an overall height between 25.4 and 38.1 mm. The terminal ends 715 can have a height or length 720 between 7.62 mm and 20.3 mm. The height or length 725 of a sensing element 730 can be between 5.0 mm and 17.8 mm. In some embodiments, the sensing element 730 can have a thickness 735 between 0.5 mm and 1.27 mm. In some embodiments, the space 740 between adjacent sensing elements 730 can be between 0.5 mm and 1.27 mm. In some embodiments, the bridge elements 745 can be configured at an angle 750 relative to one another. The angle 750 can be between 0 and 90 degrees.

FIG. 7C is a cross-sectional front view of the sensor head 705 from the perspective of line A-A of FIG. 7B. As shown in FIG. 7C, the sensor head 705 can include a plurality of holes in the sensing element 730. For example, the sensing element 730 can include a first pair of holes 755 having a diameter between 0.5 mm and 1.78 mm. The holes 755 can be configured for the bridge elements 745 to pass through the sensing element 730. In this way, contact of the bridge element 745 and the sensing element 730 can be eliminated so that the bridge element 745 and the sensing element 730 are electrically isolated from one another. The sensing element 730 can also include a second set of holes 760 having a diameter between 0.5 mm and 2.54 mm. In some embodiments, the holes 760 can have a larger diameter on one side of the sensing element 730 and a smaller diameter on an opposite side of the sensing element 730. In this way, the bridge element 745 can extend at an angle between adjacent sensing elements 730.

In some embodiments, the bridge element 745 can be a dimensional positioning element that is temporarily included to maintain spacing of the sensing elements of the first and second electrodes during manufacturing of the sensor head. In such an embodiment, the bridge element 745 can be removed via grinding or milling after the sensor head is configured within a seal assembly of the sensor. Alternatively, in some embodiments, the bridge element 745 can include an electrically isolating material such as plastic, glass, or ceramic material. In such embodiments, the bridge element 745 may remain in place and may not be removed when the sensor head is configured within a seal assembly of the sensor. In some embodiments, the seal can be a mounting or a holder of the sensor head configurations described herein. In some embodiments, the bridge element 745 can remain in place without configuring the sensor head within a seal assembly. For example, the bridge element 745 can remain in place as a dimensional positioning element when the sensor head is provided within an open container. Alternatively, the bridge element 745 can be removed when the sensor head is provided within an open container. A variety of configurations of the sensor head, including the bridge element 745 and removing the bridge element 745 can be envisioned.

Figure 8B:
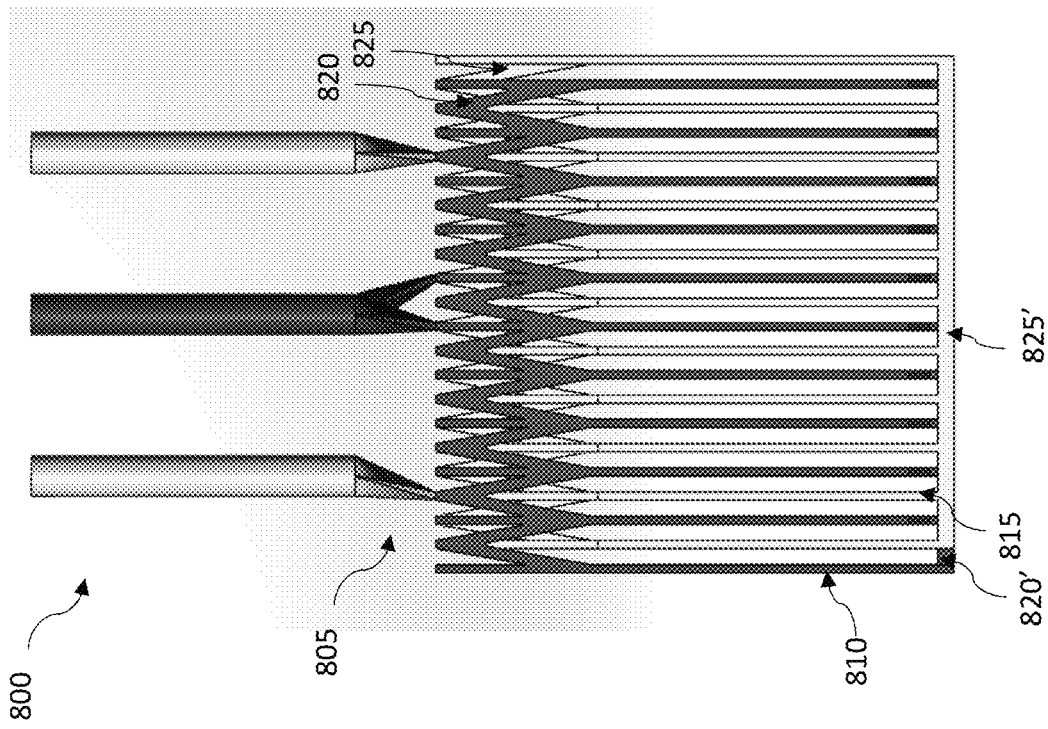
FIGS. 8A and 8B are diagrams illustrating another embodiment of a sensor described herein according to the subject matter provided herein.
Figure 8A:
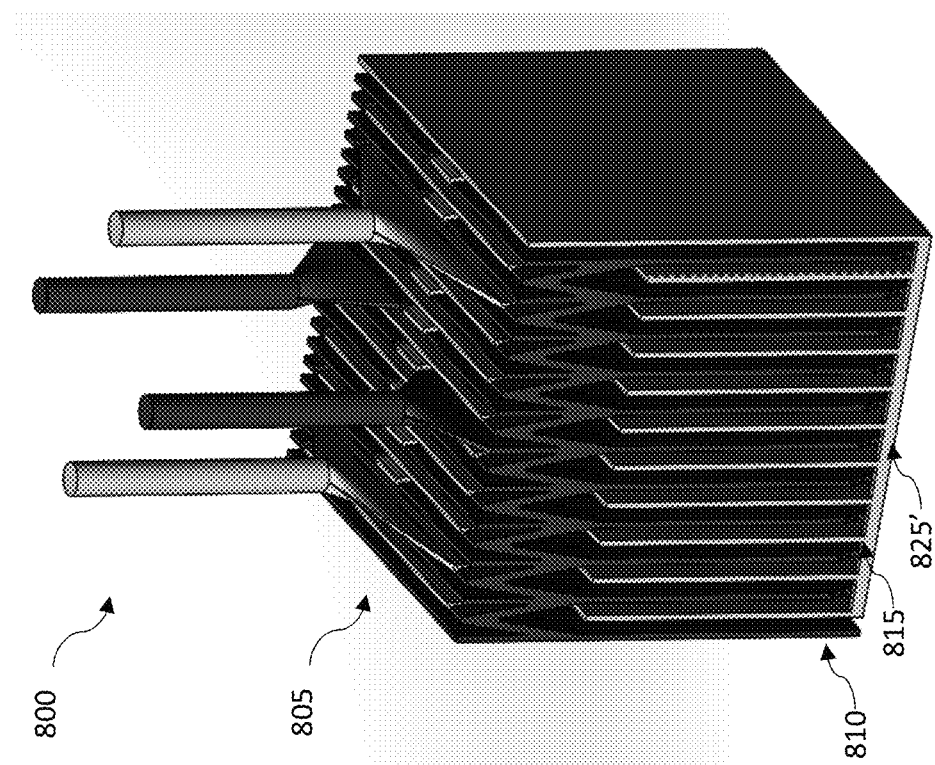

FIGS. 8A and 8B are diagrams illustrating another embodiment of a sensor 800 described herein according to the subject matter provided herein. FIG. 8A is an isometric view of a sensor 800 and sensor head 805. As shown in FIGS. 8A and 8B, the sensor head 805 can include square-shaped sensor elements 810. The sensor elements 810 included in a first electrode and sensor elements 815 included in a second electrode can be interleaved together in a planar manner so as to form a sensor head 805 with a cubic shape. FIG. 8B illustrates a side view of the sensor 800 and sensor head 805. In the embodiments, shown in FIGS. 8A and 8B, the bridge elements 820 coupled to the sensing elements 810 of the first electrode can be interleaved with the bridge elements 825 coupled to the sensing elements 815 of the second electrode.

As shown in FIGS. 8A and 8B, the second electrode formed from sensing elements 815 and bridge elements 825 can also include a bridge element 825' formed on the bottom of the sensor head 805 on opposing edges of each sensing element 815. The bridge element 825 can be arranged at the upper portion of the sensor head 805 and can be centrally located in the upper portion of the sensor head 805 between opposing edges of the sensing elements 815. The first electrode formed from the sensing elements 810 and bridge elements 820 can also include a bridge element 820' formed at the bottom portion of the sensor head 805. The bridge element 820 can be located in the upper portion of the sensor head 805 at opposing edges of the sensing elements 810.

Figure 9:
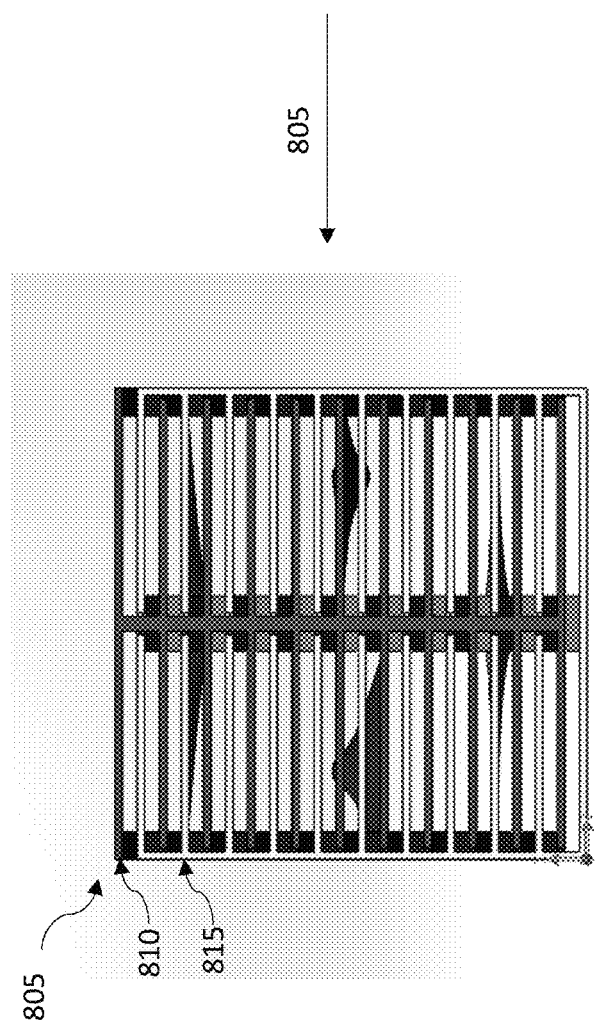
FIG. 9 is a diagram illustrating a bottom view of the embodiment of the sensor head of FIGS. 8A and 8B described according to the subject matter provided herein.

FIG. 9 is a diagram illustrating a bottom view of the embodiment of the sensor head 805 of FIGS. 8A and 8B described according to the subject matter provided herein. A fluid 905 can flow through the gaps formed by the spacing of the sensor elements 810, 815 in the sensor head 805.

Figures 10A, 10B:
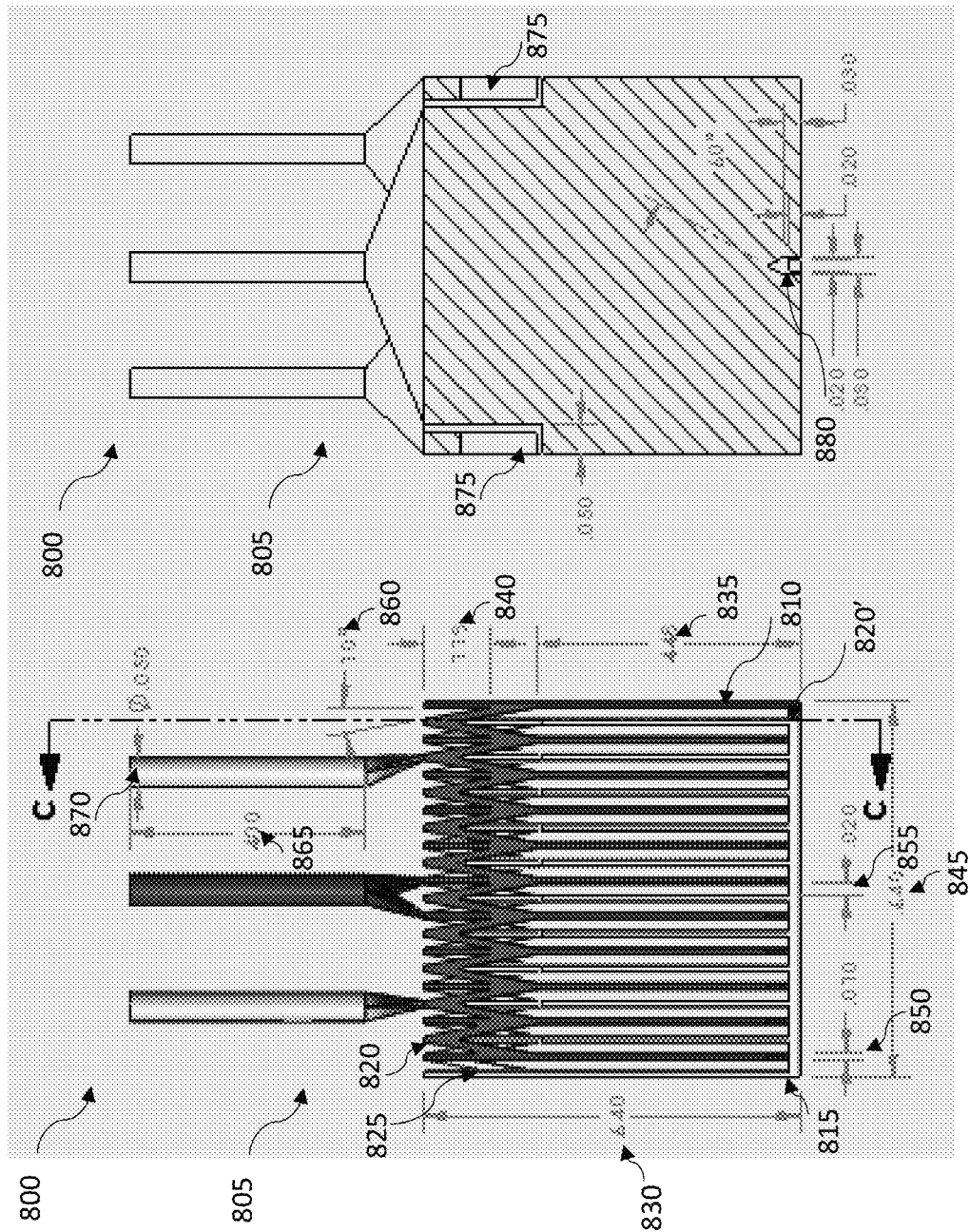
FIGS. 10A and 10B are diagrams illustrating a side view and a cut-away view, respectively, of the sensor of FIGS. 8A and 8B described according to the subject matter provided herein.

FIGS. 10A and 10B are diagrams illustrating a side view and a cut-away front view, respectively, of the sensor 800 of FIGS. 8A and 8B described according to the subject matter provided herein. As shown in FIG. 10A, the height 830 of the sensing elements 810, 815 (including the bridge element region 840) can be between 7.6 mm and 25.4 mm and can include. The height 835 of the sensing elements 810, 815 (excluding the bridge element region 840) can be between 7.6 mm and 20.3 mm. The bridge element region 840 can have a height between 1.2 mm and 4.45 mm. The width 845 of the sensing elements 810, 815 can be between 7.6 mm and 20.3 mm. The thickness 850 of the sensing elements 810, 815 can be 0.12 mm to 3.81 mm. The space or gap 855 between the sensing elements 810, 815 can be 0.25 mm to 0.76 mm. The angle 860 at which the bridge elements 820, 825 extend away from a respective sensing element 810, 815 can be between 5 degrees and 25 degrees. The height 865 of the terminal ends 870 can be between 5.0 mm and 15.2 mm.

FIG. 10B is a cut-away front view of the sensor 800 taken from the perspective of line C-C of FIG. 10A. As shown in FIG. 10B, the sensor head 805 can include a bridge element rail 875. The bridge element rail 875 can provide structural integrity to the bridge elements 820, 825 Also shown in FIG. 10B, the sensor head 805 can include a notch 880. The notch can be formed in one or more of the sensing elements 810, 815. The notch 880 can provide an electrically isolating passage for bridge element 820' to pass through the sensing element 815 along which line C-C is located.

Figure 11:
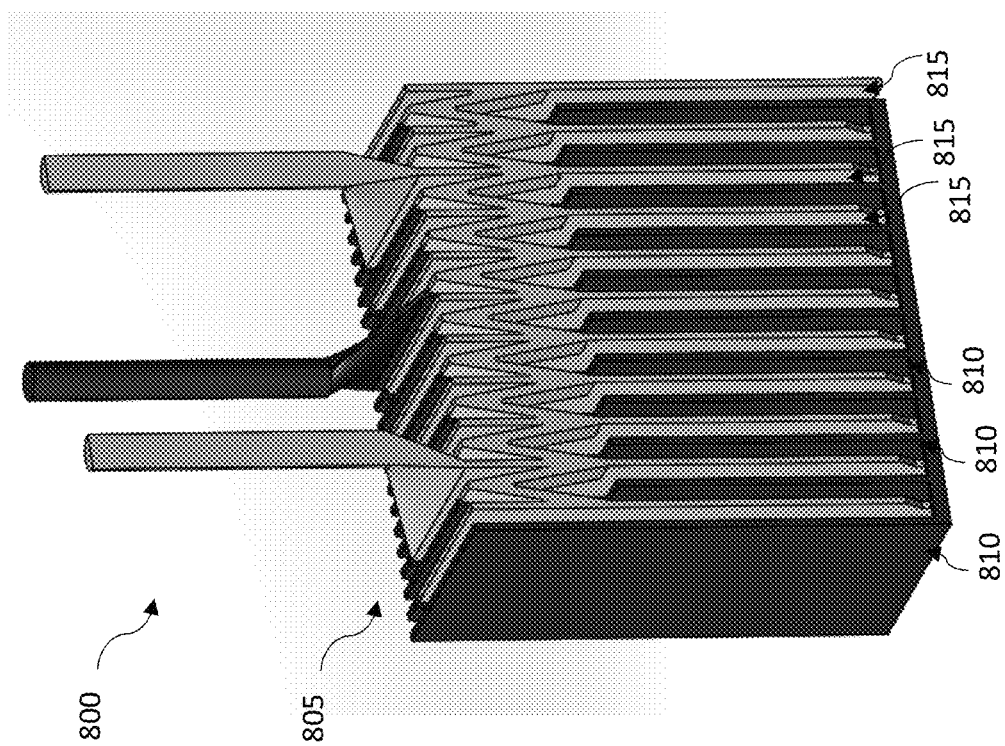
FIG. 11 is a diagram illustrating an isometric side view of the embodiment of the sensor of FIGS. 8A-10B described according to the subject matter provided herein.

FIG. 11 is a diagram illustrating an isometric side view of the embodiment of the sensor 800 of FIGS. 8A-10B described according to the subject matter provided herein. As shown in FIG. 11, the sensor head 805 can include a series of nested and interleaved sensing elements 810, 815.

FIGS. 12A and 12B are diagrams illustrating isometric views of another embodiment of a sensor described according to the subject matter provided herein. As shown in FIG. 12A, the sensor 1200 can include housing or casing 1210 surrounding the sensor head 1205. The housing 1210 can include a plurality of holes 1215 for fluid to flow though the housing 1210 and into the sensor head 1205 where it can flow between spaces or gaps between the sensing elements 1220 and 1225. The sensing elements 1220 and 1225 can be formed as cylindrically-shaped plates that concentrically arranged with respect to one another and are electrically coupled via their respective bridge elements 1230 and 1235. In addition, the sensor 1200 can be arranged with respect to a fluid 1240 flowing into the sensor, such that a maximal volume of the fluid 1240 can pass over the sensing elements 1220, 1225.

As shown in FIG. 12B, the sensor 1200 can also include terminal ends 1245 and 1250. The terminal end 1245 can be included in a first electrode and can be coupled to the sensing elements 1225. The terminal end 1250 can be included in a second electrode and can be coupled to the sensing elements 1220. A base 1250 can be positioned at an inferior position of the sensor 1200 (relative to the flow of the fluid 1240) and the sensing elements 1220, 1225 can be coupled to the base 1250. The base 1250 can provide structural integrity to the sensor head 1205.

FIGS. 13A and 13B are top and side views, respectively, of the sensor of FIGS. 12A and 12B described according to the subject matter provided herein. As shown in FIG. 13A, the sensor can include a housing 1210 and a concentric arrangement of sensing elements 1220, 1225. The sensing elements 1220 of a first electrode can be coupled via a bridge element 1230 and the sensing elements of a second electrode 1225 can be coupled via the bridge element 1235. The cylinder-shaped sensor 1200 can include variously dimensioned radiuses for each of the concentric features as shown in FIG. 13A. The thickness of the bridge element 1230 and/or 1235 can be between 0.25 mm and 0.76 mm.

As shown in FIG. 13B, the sensor 1200 can have a diameter that is between 12.7 mm and 20.3 mm. The sensor 1200 can have a height that is between 8.8 mm and 17.7 mm. The terminal ends 1245 and 1250 can each have a length that is between 3.8 mm and 10.1 mm. The terminal ends 1245 and 1250 can have a thickness that is between 0.38 mm and 1.20 mm. The holes 1215 can have a radius that is between 0.12 and 0.50 mm.

Figure 14B:
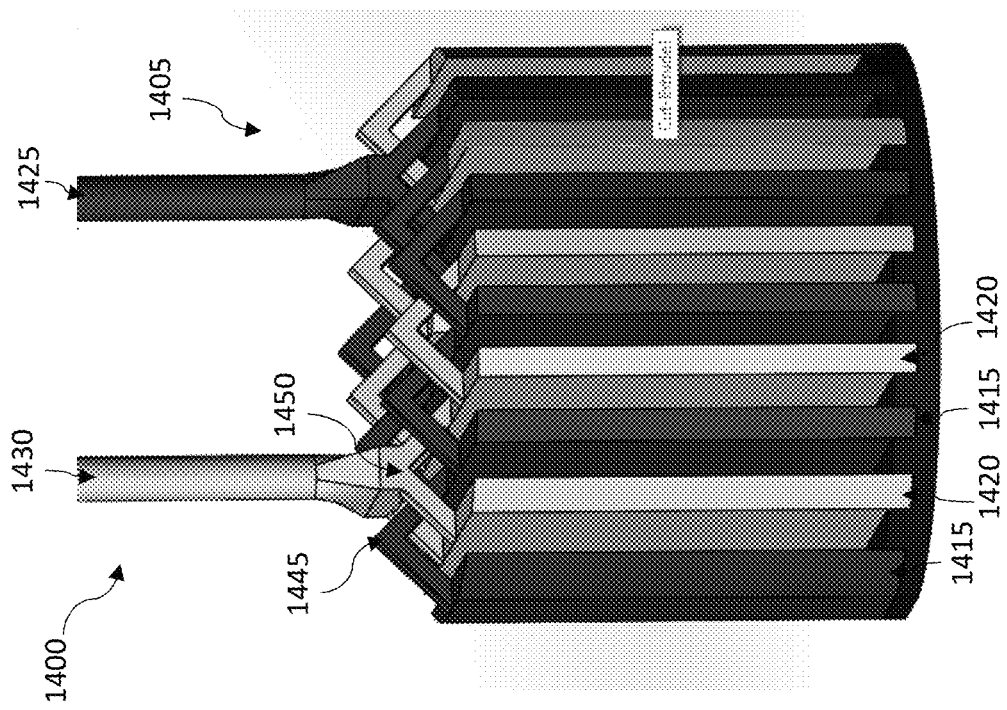
FIGS. 14A and 14B are diagrams illustrating isometric side views of another embodiment of a sensor described according to the subject matter provided herein.
Figure 14A:
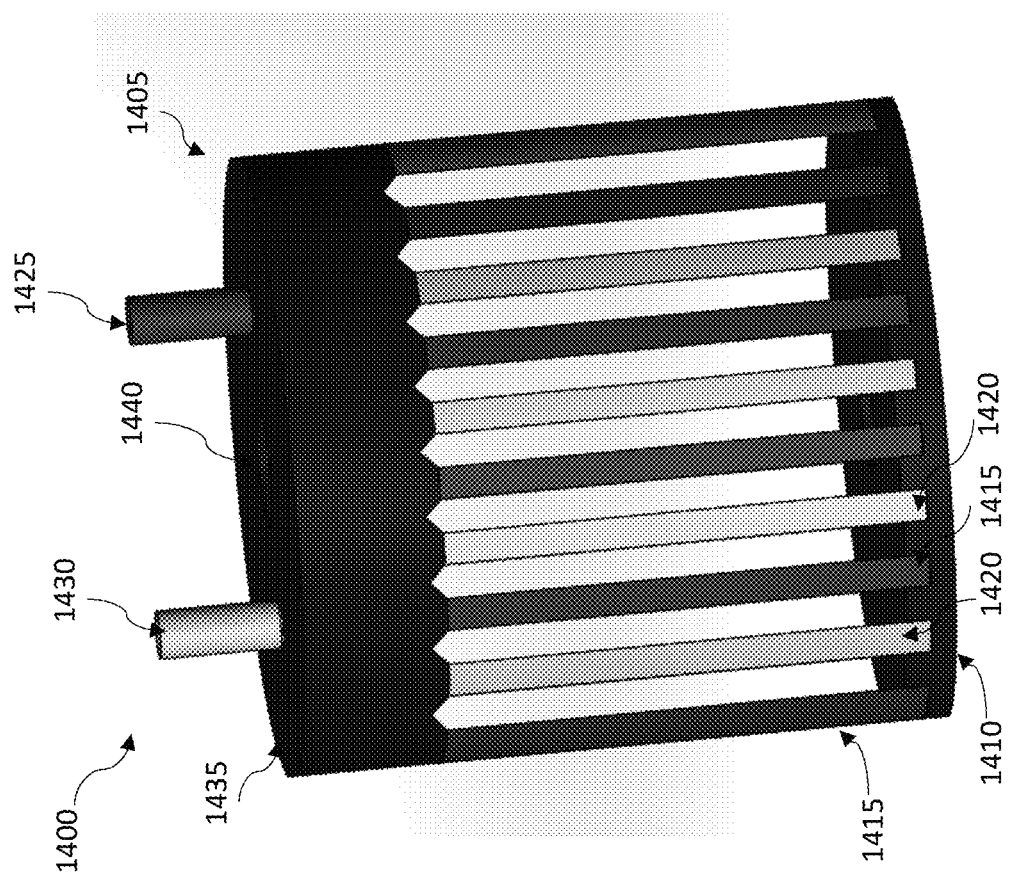

FIGS. 14A and 14B are diagrams illustrating isometric side views of another embodiment of a sensor described according to the subject matter provided herein. As shown in FIG. 14A, the sensor 1400 can include a sensor head 1405 and a base 1410. A plurality of pairs of sensing elements 1415, 1420 can be coupled to the base 1410 and can be reinforced by the coupling with the base 1410. The plurality of sensing elements 1415 can form a first electrode of the sensor 1400 that can be further coupled to a terminal end 1425 of the first electrode. Similarly, the plurality of sensing elements 1420 can form a second electrode of the sensor 1400 that can be further coupled to a terminal end 1430 of the second electrode. A header 1435 can be coupled to the plurality of pairs of sensing elements 1415, 1420 and can secure the plurality of pairs of sensing elements 1415, 1420 in the sensor head 1405. The header 1435 can also include a hole 1440. The hole 1440 can receive a measurement component, such as a thermocouple, that can extend through the hole and into a space between the sensing elements 1415, 1420. In this way, a temperature of a fluid flowing through the sensor 1400 can be measured.

As shown in FIG. 14B, the header 1435 shown in FIG. 14 is removed to illustrate additional detail of the bridge elements 1445, 1450. In the embodiment, shown in FIG. 14B, the bridge element 1445 can couple adjacent sensing elements 1415 and a plurality of bridge elements 1445 can be configured to couple multiple pairs of sensing elements 1415. Similarly, the bridge element 1450 can couple adjacent sensing elements 1420 and a plurality of bridge elements 1450 can be configured to couple multiple pairs of sensing elements 1420. The bridge elements 1445, 1450 can be formed atop the pairs of sensing elements 1415, 1420. Anyone of the bridge elements 1445, 1450 can be formed to couple with a terminal end 1425, 1430, respectively.

Figure 15:
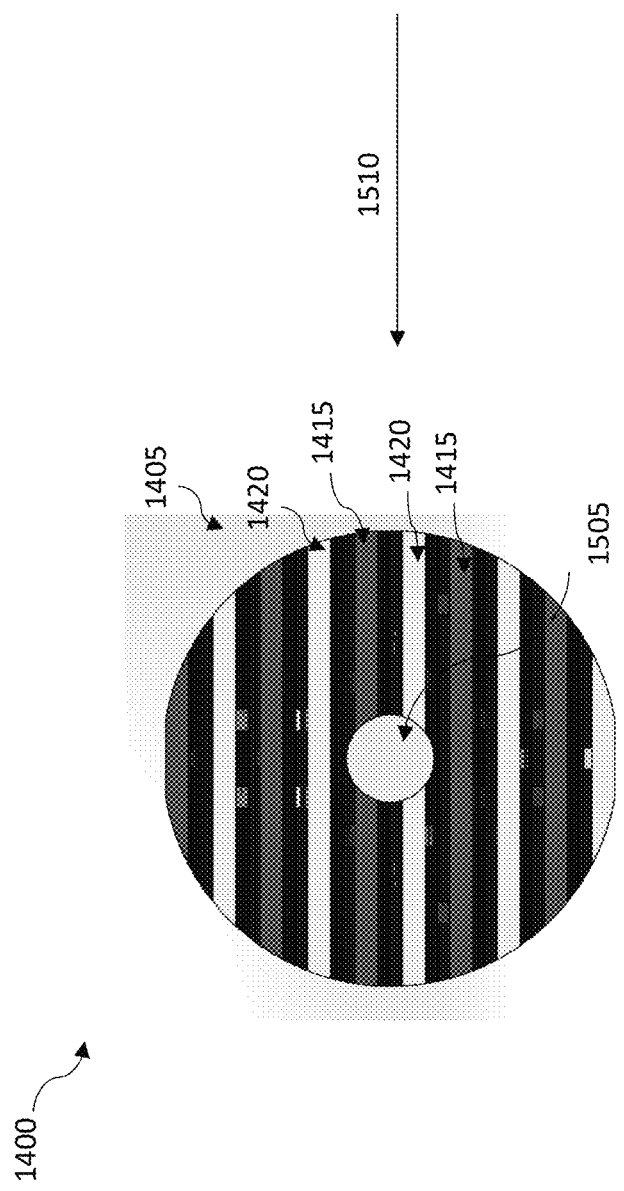
FIG. 15 is a diagram illustrating a bottom view of the sensor of FIGS. 14A and 14B described according to the subject matter provided herein.

FIG. 15 is a diagram illustrating a bottom view of the sensor of FIGS. 14A and 14B described according to the subject matter provided herein. As shown in FIG. 15, the sensor 1400 can include a hole 1505 between the plurality of sensing element pairs 1415, 1420. The sensor 1400 can also be configured for a fluid 1510 to flow through the gaps or spaces between the sensing element pairs 1415, 1420.

FIGS. 16A-16C are diagrams illustrating top, side, and close up views, respectively, of the sensor of FIGS. 14A and 14B described according to the subject matter provided herein. As shown in FIG. 16A, the header 1435 can include a hole 1440. The hole 1440 can have a diameter between 1.9 mm and 3.8 mm. The header 1435 can also include holes for the terminal ends 1425, 1430. The holes for the terminal ends 1425, 1430 can have a diameter between 0.76 mm and 1.78 mm. The radius of the header 1435 can be between 5.0 mm and 13.0 mm As shown in FIG. 16B, the sensor head 1405 can have a height between 12.0 mm and 20.3 mm. The header 1435 can have a height between 2.5 mm and 5.1 mm. The plurality of sensing element pairs 1415, 1420 can have a height between 7.6 mm and 17.8 mm. Each of the sensing elements 1415, 1420 can have a thickness between 0.50 mm and 1.27 mm. The spacing or gap between each of the sensing elements 1415, 1420 can be between 0.50 mm and 1.27 mm.

As shown in FIG. 16C, a detailed view of the bridge element region of the sensor head 1405 is shown with the header 1435 removed for clarity. As shown in FIG. 16C, the bridge elements 1445, 1450 can have a height 1605 between 1.27 mm and 3.17 mm. The angle 1610 of the bridge elements 1445, 1450 relative to the sensing element to which they are coupled can be between 25 degrees and 75 degrees. The apex height 1615 of the bridge elements 1445, 1450 can be between 3.8 mm and 10.2 mm. The thickness 1620 of the bridge elements 1445, 1450 can be between 3.8 mm and 10.2 mm. The diameter 1625 of the terminal ends 1425, 1430 can be between 0.76 mm and 1.78 mm.

Figure 17:
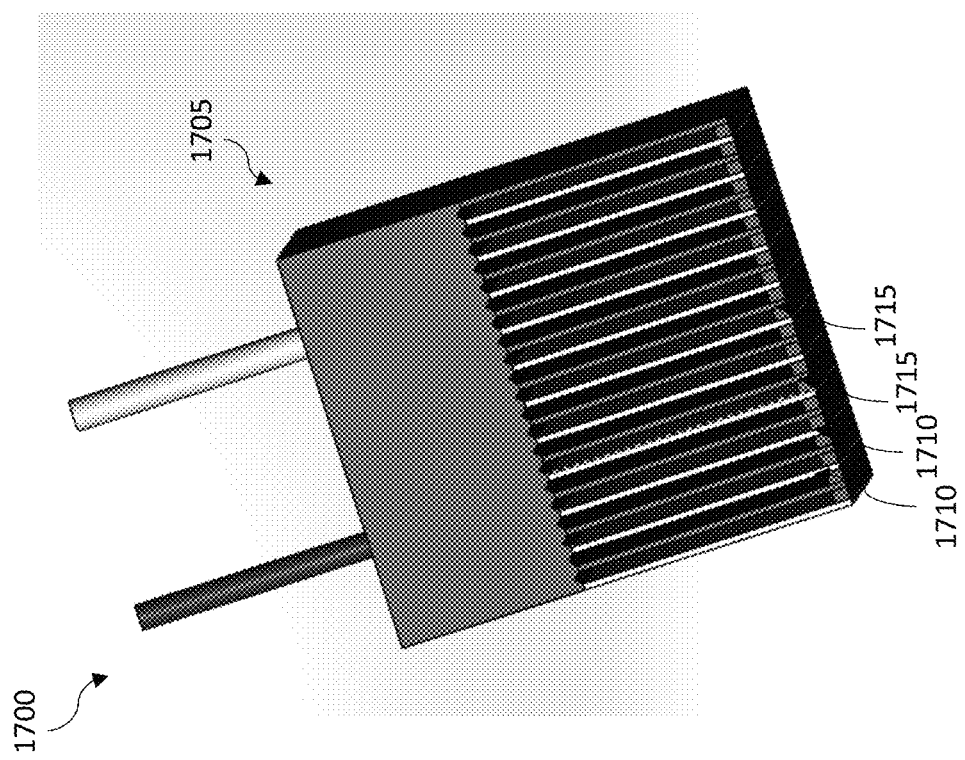
FIG. 17 is a diagram illustrating an isometric side view of an additional embodiment of a sensor described according to the subject matter provided herein.

FIG. 17 is a diagram illustrating an isometric side view of an additional embodiment of a sensor 1700 described according to the subject matter provided herein. As shown in FIG. 17, the sensor 1700 can include a sensor head 1705 having a plurality of square-shaped sensing elements 1710, 1715 that can be interleaved with one another and can be arranged to provide a space or gap between adjacent sensing elements 1710, 1715.

Figure 18:
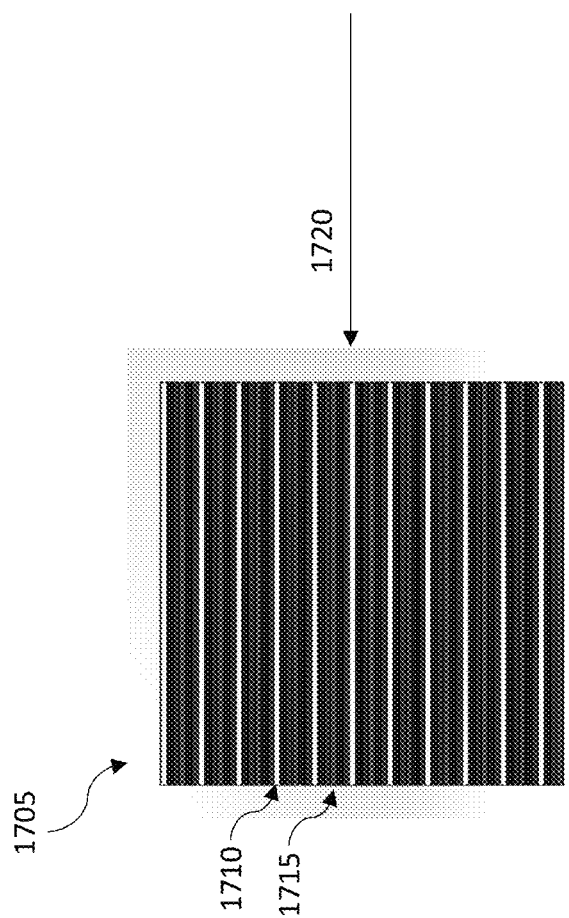
FIG. 18 is a diagram illustrating a bottom view of the sensor head of FIG. 17 described according to the subject matter provided herein.

FIG. 18 is a diagram illustrating a bottom view of the sensor head 1705 of FIG. 17 described according to the subject matter provided herein. As shown in FIG. 18, a fluid 1720 can flow into the sensor head 1705 and can pass through the spaces or gaps formed between the sensing elements 1710 and 1715.

Figure 19B:
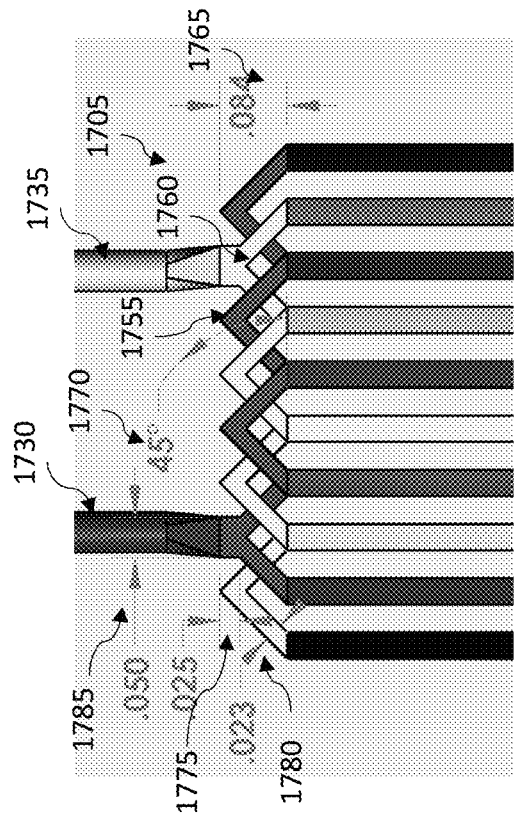
FIGS. 19A-19B are diagrams illustrating side and close-up views of the sensor of FIG. 17 described according to the subject matter provided herein.
Figure 19A:
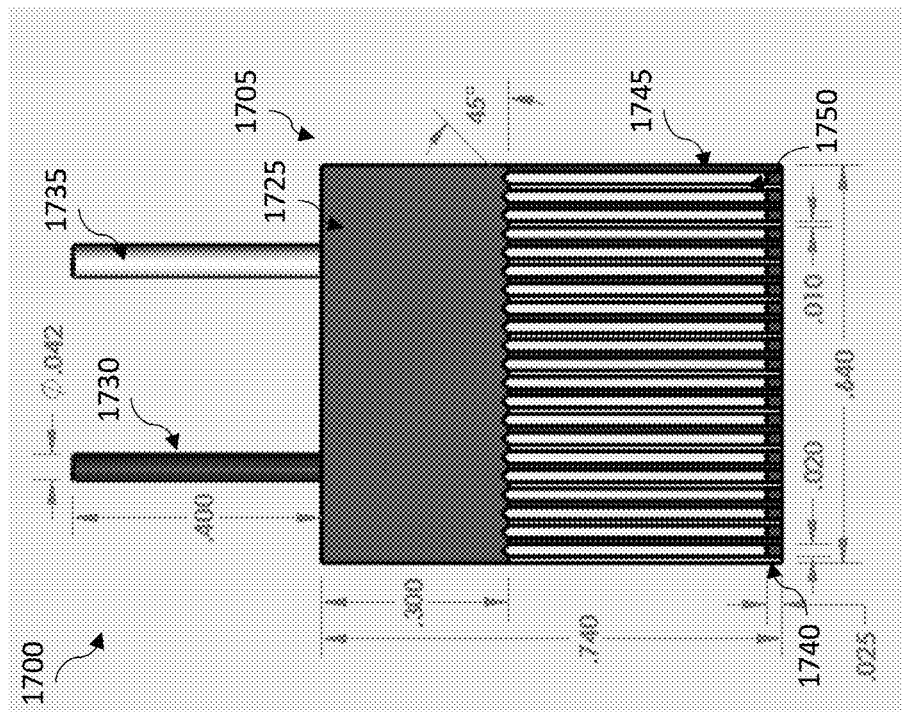

FIGS. 19A-19B are diagrams illustrating side and close-up views of the sensor 1700 of FIG. 17 described according to the subject matter provided herein. As shown in FIG. 19A, the sensor 1705 can include a height between 12.7 mm and 25.4 mm. The sensor head 1705 can have a width between 7.6 mm and 22.8 mm. The sensor head 1705 can include a header 1725 in which the terminal ends 1730, 1735 can be secured and can extend there through. The header 1725 can have a height between 3.8 mm and 12.7 mm. The terminal ends 1730, 1735 can have a diameter between 7.6 mm and 15.3 mm. The terminal ends 1730, 1735 can have a height between 5.0 mm and 15.3 mm. The sensor head 1705 can also include a base 1740 attached to the plurality of sensing elements 1745, 1750. The base 1740 can have a height between 0.38 mm and 1.0 mm. The width of the sensing elements 1745, 1750 can be between 1.27 mm and 5.10 mm. The spacing between the sensing elements 1745, 1750 can be between 0.254 mm and 1.10 mm.

As shown in FIG. 19B, a detailed view of the bridge element region of the sensor head 1705 is shown with the header 1725 removed for clarity. As shown in FIG. 19B, the bridge elements 1755, 1760 can have a height 1765 between 1.27 mm and 3.18 mm. The angle 1770 of the bridge elements 1755, 1760 relative to the sensing element to which they are coupled can be between 25 degrees and 75 degrees. The apex height 1775 of the bridge elements 1755, 1760 can be between 3.8 mm and 10.2 mm. The thickness 1780 of the bridge elements 1755, 1760 can be between 3.8 mm and 10.2 mm. The diameter 1785 of the terminal ends 1730, 1735 can be between 0.76 mm and 1.78 mm.

Figure 20B:
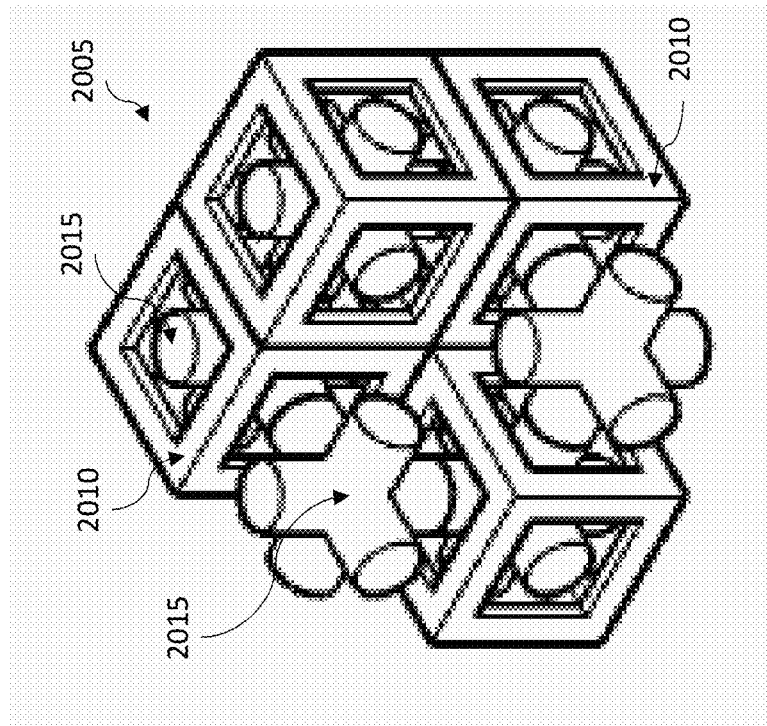
FIGS. 20A-20B are diagrams illustrating another embodiment of a sensor described according to the subject matter provided herein.
Figure 20A:
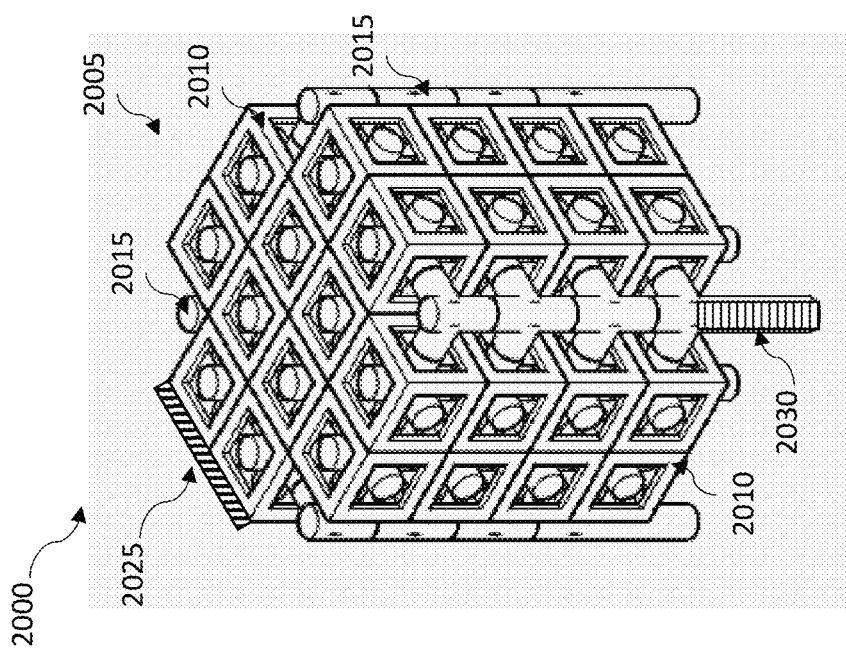

FIGS. 20A-20B are diagrams illustrating another embodiment of a sensor 2000 described according to the subject matter provided herein. As shown in FIG. 20A, in an embodiment, the sensor 2000 can be formed as a matrix or lattice structure. A first electrode can include a plurality of sensing elements 2010 coupled to one another and forming an outer structure around a plurality of sensing elements 2015 forming an inner structure. The plurality of sensing elements 2015 can form the second electrode of the sensor head 2005. The design of the sensor 2000 can advantageously increase surface area of the first and second electrode formed by the sensing elements 2010 and 2015 so that fluid passing through the sensor 2000 is spread across a maximal surface area of the sensor head 2004.

In some embodiments, one or more portions of the first electrode formed from sensing elements 2010 can include a conductive coating 2025. In some embodiments, one or more portions of the second electrode formed from sensing elements 2015 can include a conductive coating 2030. In some embodiments, one or more portions of the first electrode formed from sensing elements 2010 and/or one or more portions of the second electrode formed from sensing elements 2015 can be formed from a non-conductive material. In some embodiments, the non-conductive coating can include a ceramic material.

FIG. 20B illustrates a detailed view of the sensor head 2005. As shown, sensing elements 2010 and 2015 can be formed together in a unibody construction having a matrix or lattice-like shape. Although the sensing elements 2010 and 2015 are shown with square and orthogonally-oriented or axial shapes/orientations, a variety of geometric designs can be envisioned incorporating a first electrode structure of a first set of sensing elements within an outer structure of a second electrode formed from a second set of sensing elements surrounding the first set of sensing elements of the first electrode.

Figure 21:
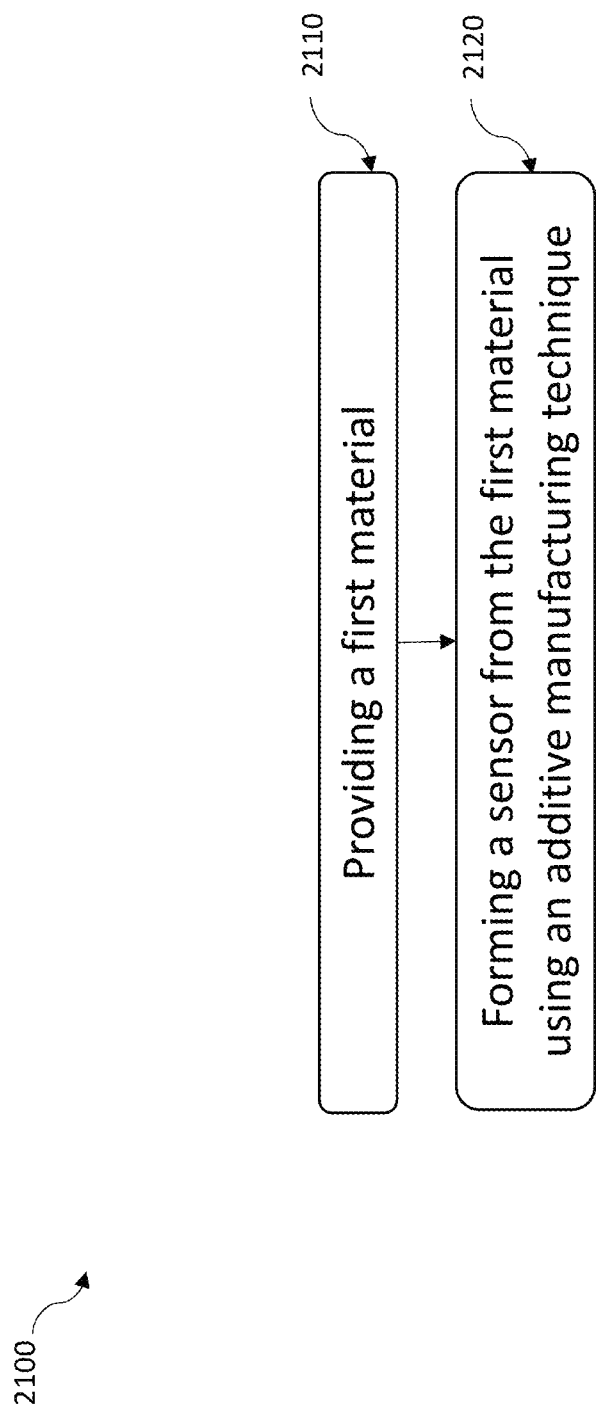
FIG. 21 is a flow chart illustrating an embodiment of a method for manufacturing a sensor described according to the subject matter provided herein.

FIG. 21 is a flow chart illustrating an embodiment of a method 2100 for manufacturing a sensor described according to the subject matter provided herein. At 2110, a first material. The first material can include a metal or a ceramic material. In some embodiments, a second material can be blended with the first material. In some embodiments, the first material or the second material can be a powered material.

At 2120, a sensor can be formed from the first material using an additive manufacturing technique. The sensor can include a sensor as described in the embodiments provided herein. The additive manufacturing technique can include direct laser melting, direct metal laser melting, binder jetting, material jetting, powder bed fusion, or digital light processing. In some embodiments, a first portion of the sensor can be formed from the first material and a second portion of the sensor can be formed from the second material. Using the additive manufacturing technique, the sensor can be formed to have a unibody, one piece, integral construction that is not assembled from multiple pieces. An additional benefit of forming the sensor via additive manufacturing techniques is that smaller sized sensors can be produced with reduced feature dimensions that existing sensor designs which require assembly of separate components to form the sensor. Precisely controlling the dimensions of features of the sensor using additive manufacturing techniques can enhance the efficacy of some components of the sensor, such as the holes, pass-throughs, as well as the spacing and gaps between sensing elements that can receive a fluid across a greater surface area than legacy sensors which have been assembled from multiple components.

In some embodiments, the method can further include applying a conductive coating to a ceramic material.

The improved sensor and method of manufacturing described herein address the technical problem of increasing the measurement sensitivity and throughput of a sensor for use in monitoring a fluid. Using additive manufacturing techniques, the sensor described herein can provide exemplary technical effects of a smaller sensor design that can be used in a wider variety of applications for fluid monitoring. The sensor and method of manufacturing described herein can improve the usable surface area of the sensing elements to ensure a maximal amount of fluid contacts the sensing elements. This can increase the accuracy of the sensor and broaden its usage over a larger number of applications than existing sensors which are assembled from multiple components. In addition, the sensor and method of manufacture described herein can enable rapid prototyping of new sensor designs without incurring excessive inventories or parts in advance of a final design.

Certain exemplary embodiments have been described to provide an overall understanding of the principles of the structure, function, manufacture, and use of the systems, devices, and methods disclosed herein. One or more examples of these embodiments have been illustrated in the accompanying drawings. Those skilled in the art will understand that the systems, devices, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention. Further, in the present disclosure, like-named components of the embodiments generally have similar features, and thus within a particular embodiment each feature of each like-named component is not necessarily fully elaborated upon.

Approximating language, as used herein throughout the specification and claims, may be applied to modify any quantitative representation that could permissibly vary without resulting in a change in the basic function to which it is related. Accordingly, a value modified by a term or terms, such as "about," "approximately," and "substantially," are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

One skilled in the art will appreciate further features and advantages of the invention based on the above-described embodiments. Accordingly, the present application is not to be limited by what has been particularly shown and described, except as indicated by the appended claims. All publications and references cited herein are expressly incorporated by reference in their entirety.

What is claimed is:

1. A sensor comprising: a sensor head having a unibody construction and comprising a first electrode and at least one second electrode, the first electrode comprising
   a first pair of sensing elements coupled to each other via at least one first bridge element extending from a first sensing element to a second sensing element, the first sensing element and the second sensing element included in the first pair of sensing elements, and
   the at least one second electrode comprising
   a second pair of sensing elements interleaved with the first pair of sensing elements, the second pair of sensing elements coupled to each other via at least one second bridge element extending from a third sensing element to a fourth sensing element, the third sensing element and the fourth sensing element included in the second pair of sensing elements.

2. The sensor of claim 1, wherein the at least one first bridge element extends through a pass-through feature of the third sensing element and the at least one second bridge element extends through a pass-through feature of the second sensing element.

3. The sensor of claim 1, wherein the sensor includes a housing and a header.

4. The sensor of claim 1, wherein the sensor comprises a base coupled to the first electrode and the second electrode.

5. The sensor of claim 1, wherein the sensor comprises a thermocouple positioned between the first electrode and the second electrode.

6. The sensor of claim 1, wherein the sensor is an impedance sensor.

7. The sensor of claim 6, wherein the impedance sensor is installed in at least one of a combustion engine, a gear box, a gas turbine, a compressor, or a hydraulic system.

8. The sensor of claim 7, wherein the impedance sensor is configured in an oil and gas production environment.

9. The sensor of claim 1, wherein the first electrode or the second electrode are formed from a non-conductive material and the first electrode or the second electrode are coated with a conductive coating.

10. The sensor of claim 9, wherein the non-conductive material is a ceramic.

11. The sensor of claim 1, wherein the first electrode and the second electrode are interleaved in a planar manner to form a cylindrical shape.

12. The sensor of claim 1, wherein the first electrode and the second electrode are interleaved in a planar manner to form a cubic shape.

13. The sensor of claim 1, wherein the first electrode and the second electrode are interleaved in a concentric manner to form a cylindrical shape.

14. The sensor of claim 1, wherein the sensor comprises a plurality of gaps between adjacent sensing elements of the first pair of sensing elements and the second pair of sensing elements.

15. The sensor of claim 14, wherein the plurality of gaps are configured for a fluid to flow through the sensor.

16. The sensor of claim 15, wherein the fluid is a lubricant, water, an oil, or a coolant.

17. A method of manufacturing comprising:
   providing a first material; and
   forming a sensor from the first material using an additive manufacturing technique, the sensor comprising
      sensor head having a unibody construction and comprising a first electrode and at least one second electrode,
      the first electrode comprising
         a first pair of sensing elements coupled to each other via at least one first bridge element extending from a first sensing element to a second sensing element, the first sensing element and the second sensing element included in the first pair of sensing elements,
      and the at least one second electrode comprising a second pair of sensing elements interleaved with the first pair of sensing elements, the second pair of sensing elements coupled to each other via at least one second bridge element extending from a third sensing element to a fourth sensing element, the third sensing element and the fourth sensing element included in the second pair of sensing elements.

18. The method of claim 17, wherein the additive manufacturing technique includes at least one of direct laser melting, direct metal laser melting, binder jetting, material jetting, powder bed fusion, or digital light processing.

19. The method of claim 17, wherein the first material is a metal material or a ceramic material.

20. The method of claim 19, further comprising applying a conductive coating to the ceramic material.

* * * * *